United States Patent [19]

Sysko et al.

[11] Patent Number: 5,248,699
[45] Date of Patent: Sep. 28, 1993

US005248699A

[54] SERTRALINE POLYMORPH

[75] Inventors: Robert J. Sysko, Niantic; Douglas J. M. Allen, New London, both of Conn.

[73] Assignee: Pfizer Inc., New York, N.Y.

[21] Appl. No.: 929,326

[22] Filed: Aug. 13, 1992

[51] Int. Cl.5 .................. A61K 31/135; C07C 211/42
[52] U.S. Cl. ..................................... 514/647; 564/308
[58] Field of Search ........................ 564/308; 514/647

[56] References Cited

U.S. PATENT DOCUMENTS 4,536,518  8/1985  Welch et al. .......................... 514/647
4,556,676 12/1985  Welch et al. .......................... 514/554

Primary Examiner—Richard L. Raymond
Attorney, Agent, or Firm—Peter C. Richardson; Paul H. Ginsburg; Garth Butterfield

[57] ABSTRACT

This invention relates to a novel crystalline polymorphic form of sertraline hydrochloride, (1S-cis)-4-(3,4-dichlorophenyl)-1,2,3,4 -tetrahydro-N-methyl-1-naphthalenamine hydrochloride, and to a method for preparing it.

15 Claims, 22 Drawing Sheets

BEST AVAILABLE COPY

SERTRALINE POLYMORPH

BACKGROUND OF THE INVENTION

This invention relates to a novel crystalline polymorphic form of sertraline hydrochloride, (1S-cis)-4-(3,4-dichlorophenyl)-1,2,3,4-tetrahydro-N-methyl-1-naphthalenamine hydrochloride, and to a method for preparing it.

Sertraline hydrochloride has the chemical formula $C_{17}H_{17}NCl_2 \cdot HCl$ and the following structural formula

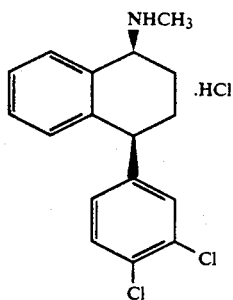

Its synthesis is described in U.S. Pat. No. 4,536,518, assigned to Pfizer Inc. Sertraline hydrochloride is useful as an antidepressant and anorectic agent, and is also useful in the treatment of chemical dependencies, anxiety-related disorders and premature ejaculation.

It has now been discovered that sertraline hydrochloride can exist as any of several novel crystalline forms, polymorphic forms, which differ from each other in their stability, physical properties, spectral data and methods of preparation. Five of these novel polymorphic forms are described in this application and are hereinafter referred to, respectively, as Form I, Form II, Form III, Form IV and Form V.

Of the five novel polymorphs referred to above, Form I, exhibits the greatest stability. Form I is characterized by a minimum of five years crystalline stability.

U.S. Pat. No. 4,536,518 does not refer to specific polymorphic crystalline forms of sertraline hydrochloride. The synthetic procedure described and exemplified in U.S. Pat. No. 4,536,518 produces the sertraline hydrochloride polymorph designated herein as Form II and described below. It does not suggest the existence of different polymorphic forms of sertraline.

SUMMARY OF THE INVENTION

This invention relates to a novel crystalline polymorph of the hydrochloride salt of (1S-cis)-4-(3,4-dichlorophenyl) -1,2,3,4-tetrahydro-N-methyl-1-naphthalenamine, sertraline hydrochloride, referred to hereinafter as Form I, which like the other crystalline forms of such compound, is useful in the treatment of depression, obesity, anxiety-related disorders, premature ejaculation, and chemical dependencies and addictions, and which is suitable for use as the active ingredient of a commercial pharmaceutical product. This novel crystalline polymorph melts at about 219° C. [215° to 225° C.], and exhibits a Characteristic X-ray powder defraction pattern with characteristic peaks expressed in degrees $2\theta$ at 7.1, 12.7, 14.1, 15.3, 15.7, 21.2, 23.4 and 26.3 as depicted in FIG. 1. A discussion of the theory of X-ray powder defraction patterns can be found in Stout & Jensen, *X-Ray Structure Determination; A Practical Guide,* Mac Millian Co., New York, N.Y. (1968).

This invention also relates to a crystalline polymorph of the hydrochloride salt of (1S-cis)-4-(3,4-dichlorophenyl)-1,2,3,4-tetrahydro-N-methyl-1-naphthalenamine that is further characterized by the infrared absorption spectrum in potassium bromide pellet having the following characteristic absorption bands, expressed in reciprocal centimeters:

3100–3000(w)*; 3000–2800(m)*, 2710–2500(m); 2500–2450(m); 1585(m); 1560(m); 1470–1450(s)*; 1400(s), 1430(m); 1375(m); 1340(m) 1215(m); 1135(s); 1060(m); 1030(m); 1015(m); 955(m); 930(m); 920(m); 825(s); 800(s); 790(s); 760(s); 710(m); 700(s); 670(s). ≠*(w)=weak intensity; (m)=medium intensity; (s)=strong intensity] as depicted in FIG. 2.

This invention also relates to a crystalline polymorph of the hydrochloride salt of (1S-cis)-4-(3,4-dichlorophenyl)-1,2,3,4-tetrahydro-N-methyl-1-naphthalenamine that is further characterized by the crystal parameters obtained from single crystal X-ray crystallographic analysis set forth in Table I below.

TABLE 1

| Crystal Parameters of Form I | |
|---|---|
| Crystal size (mm) | 0.11 × 0.11 × 0.12 |
| Unit cell dimensions | a = 8.004(5)Å |
| | b = 8.372(5)Å |
| | c = 25.21(2)Å |
| | α = 90.00° |
| | β = 90.00° |
| | γ = 90.00° |
| | V = 1689.3(6)Å³ |
| Space group | P2₁2₁2₁ orthorhombic |
| Molecules/unit cell | 4 |
| Density, g/cm | 1.354 |

The unit cell dimension is defined by three parameters; length of the sides of the cell, relative angles of sides to each other and the volume of the cell. The lengths of the sides of the unit cell are defined by a, b and c. The relative angles of the cell sides are defined by α, β, and γ. The volume of the cell is defined as V. A more detailed account of unit cells can be found in Chapter 3 of Stout & Jensen, *X-Ray Structure Determination; A Practical Guide,* Mac Millian Co., New York, N.Y. (1968).

This invention also relates to a crystalline polymorph of the hydrochloride salt of (1S-cis)-4-(3,4-dichlorophenyl) -1,2,3,4-tetrahydro-N-methyl-1-naphthalenamine having a single crystal X-ray crystallographic analysis which yields atomic positions of all atoms relative to the origin of the unit cell as recited in Tables 3 through 7, and as represented in FIG. 3. Tables 3 through 7 list the parameters of atomic coordinates, and their isotropic thermal parameters, bond lengths, bond angles, anisotropic thermal parameters, and proton atom coordinates and their isotropic thermal parameters. These parameters define the absolute atomic arrangement in the crystal structure of Form I and this arrangement is depicted as the three dimensional structure in FIG. 3.

This invention also relates to a crystalline polymorph of the hydrochloride salt of (1S-cis)-4-(3,4-dichlorophenyl) -1,2,3,4-tetrahydro-N-methyl-1-naphthalenamine with a differential scanning calorimetry thermogram, as depicted in FIG. 4, having characteristic peaks at: a) from 215.65° C. to 224.65° C., having an onset at 219.87° C. and representing an absorption of 10.2 calories per gram; and b) from 242.87 to 253.13, having an onset of 246.77° C. and representing an absorption of 14.92 calories per gram, wherein said thermogram is obtained on a 1.60mg sample at a scan rate of 20.00° C. per minute.

This invention also relates to a pharmaceutical composition comprising an amount of a polymorph of Form I with any of the above characteristics effective in treating depression, anxiety-related disorders, obesity, chemical dependencies or addictions or premature ejaculation in a human, and a pharmaceutically acceptable carrier.

This invention also relates to method of treating a condition selected from depression, anxiety-related disorders, obesity, chemical dependencies and addictions and premature ejaculation in a human, comprising administering to said human an amount of a polymorph of Form I with any of the above characteristics effective in treating such condition.

This invention also relates to a method of preparing a polymorph of Form I with any of the above characteristics comprising crystallizing sertraline hydrochloride in an acidic solution using an organic solvent.

This invention also relates to a method of preparing a polymorph of Form I with any of the above characteristics comprising crystallizing sertraline hydrochloride in an acidic solution using an organic solvent, over a period of about 3 hours, at a temperature from about 20° C. to about 100° C. A preferred solvent of the invention is ethyl acetate.

DETAILED DESCRIPTION OF THE INVENTION

Figure 1:
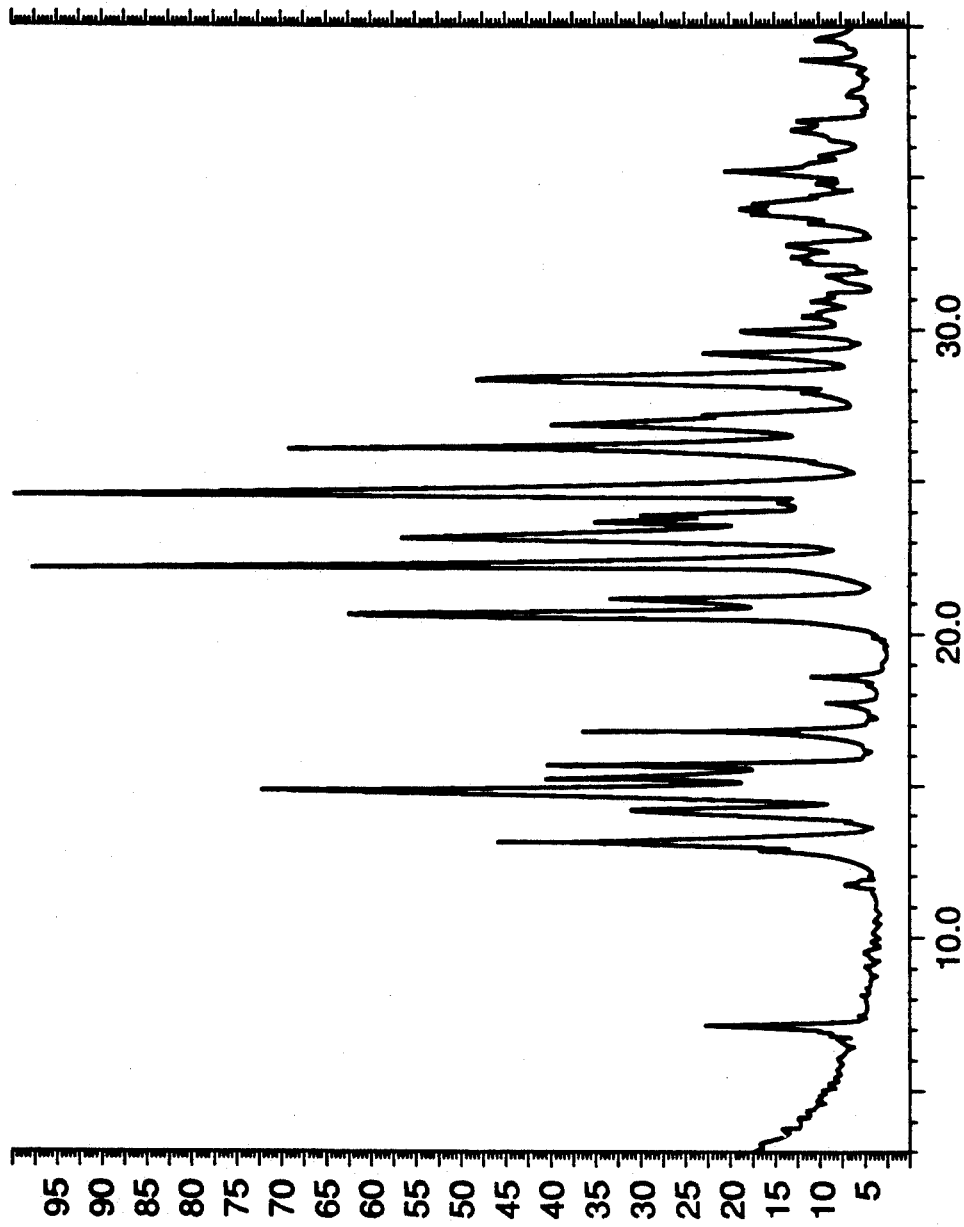
FIG. 1 is a characteristic X-ray powder diffraction pattern for Form I. (Vertical axis: Intensity (CPS); Horizontal axis: Two Theta (degrees)).
Figure 2:
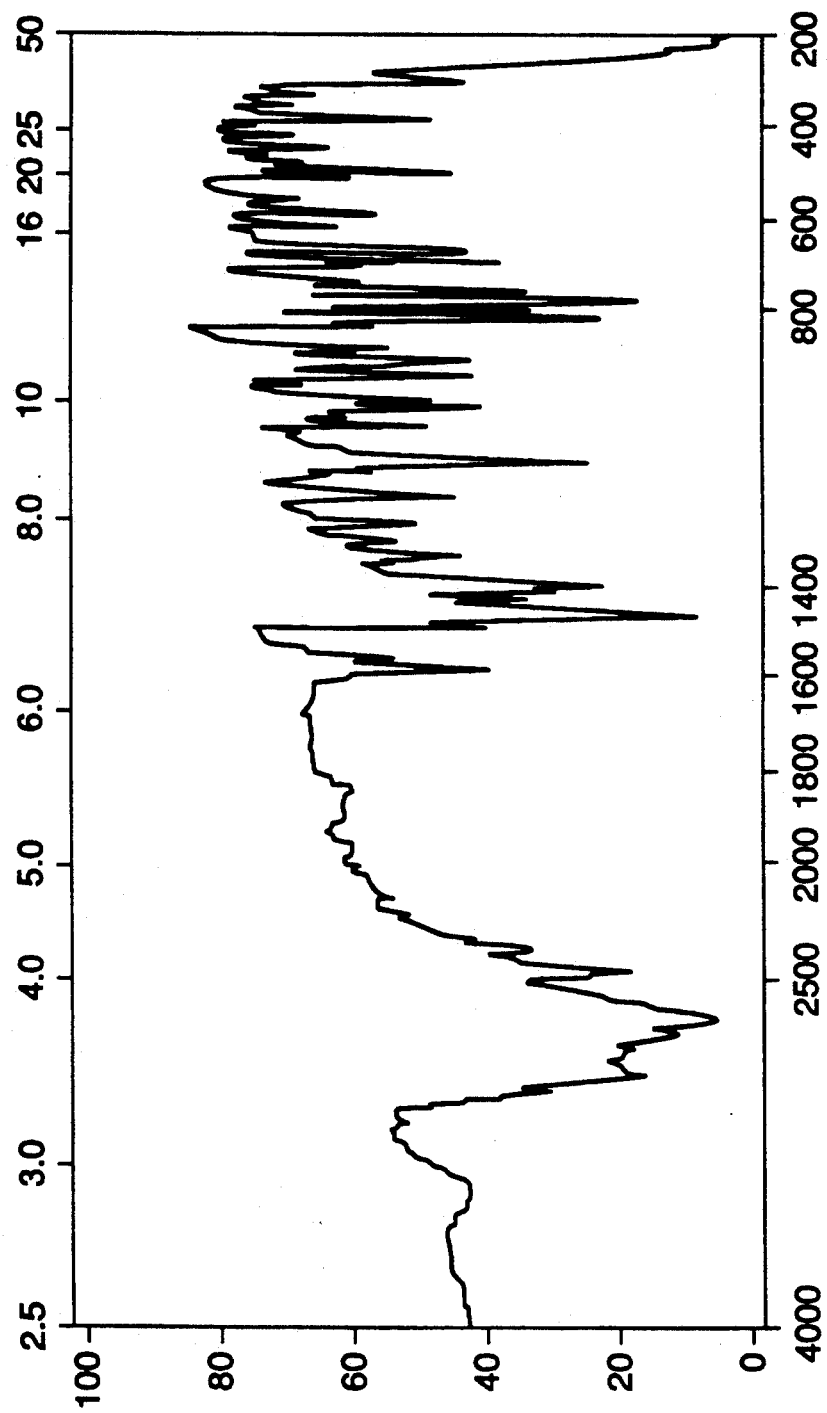
FIG. 2 is a characteristic infrared absorption spectrum in potassium bromide of Form I. (Vertical axis: Transmission (%); Upper horizontal axis: Wavelength (micrometers); Lower horizontal axis: (Wavenumber ($cm^{-1}$)).

The crystalline state of a compound can be unambiguously described by several crystallographic parameters: unit cell dimensions, space group, and atomic position of all atoms in the compound relative to the origin of its unit cell. These parameters are experimentally determined by single crystal X-ray analysis. It is possible for a compound to form more than one type of crystal. These different crystalline forms are called polymorphs. It has been discovered that there are five polymorphs of sertraline hydrochloride. This discovery was confirmed by five separate single crystal X-ray analyses. A comparison of the unit cell dimensions and space groups of these five crystalline states are given in Table 2. Plotting the atomic positions, for the five polymorphs, of the atoms derived from the single crystal X-ray analysis confirms that the crystals contain sertraline and no other molecules of crystallization or impurity. The absolute configurations of the five polymorphs are shown in FIGS. 3, 11, 12, 13 and 14. The complete single crystal X-ray experimental data used to produce the structure displayed in FIG. 3 for Form I is included in Tables 3–7. The parameters presented in the tables are measured in units commonly used by those skilled in the art. A more detailed discussion of the units of measure can be found in International Tables for X-ray Crystallography, Vol. IV, pp. 55, 99, 149 Birmingham: Kynoch Press, 1974, and G. M. Sheldrick, SHELXTL. User Manual, Nicolet Instrument Co., 1981. In Table 6, the anisotropic temperature factor exponent takes the form: $-2\pi^2(h^2a^{*2}U_{11}=\ldots=2hka^*b^*U_{12})$.

TABLE 2

Single Crystal X-Ray Crystallographic Analysis of Sertraline Hydrochloride-Crystal Parameters

|  | Form I | Form II |
|---|---|---|
| Crystal size, mm | 0.11 × 0.11 × 0.12 | 0.21 × 0.23 × 0.32 |
| Cell dimensions | a = 8.004(5)Å | a = 7.318(3)Å |
| (Å = Angstrom, | b = 8.372(5)Å | b = 7.291(3)Å |
| ° = degrees) | c = 25.21(2)Å | c = 32.470(8)Å |
|  | α = 90.00° | α = 90.00° |
|  | β = 90.00° | β = 90.00° |
|  | γ = 90.00° | γ = 90.00° |
|  | V = 1689.3(6)Å$^3$ | V = 1732.5(8)Å$^3$ |
| Space group | P2$_1$2$_1$2$_1$ | P2$_1$2$_1$2$_1$ |
|  | Orthorhombic | Orthorhombic |
| Molecules/unit cell | 4 | 4 |
| Density calculated, g/cm$^3$ | 1.354 | 1.314 |

|  | Form III | Form IV |
|---|---|---|
| Crystal size, mm | 0.006 × 0.03 × 0.04 | 0.05 × 0.08 × 0.09 |
| Cell Dimensions | a = 6.440(5)Å | a = 6.572(3)Å |
| (Å = Angstrom, | b = 10.841(7)Å | b = 10.790(4)Å |
| ° = degrees) |  | = 94.45 (6) |
|  | c = 24.82(2)Å | c = 11.88(1)Å |
|  | α = 90.00° | α = 90.00° |
|  | β = 90.00° | β = 94.45° |
|  | γ = 90.00° | γ = 90.00° |
|  | V = 1733(2)Å$^3$ | V = 839.9(9)Å$^3$ |
| Space group | p2$_1$2$_1$2$_1$ | P2$_1$ |
|  | Orthorhombic | Monoclinic |
| Molecules/unit cell | 4 | 2 |
| Density calculated, g/cm$^3$ | 1.313 | 1.349 |

|  | Form V |
|---|---|
| Crystal size, mm | 0.03 × 0.06 × 0.09 |
| Cell dimensions | a = 5.583(2)Å |
| (Å = Angstrom, | b = 9.175(4)Å |
| ° = degrees) | c = 17.04(1)Å |
|  | α = 90.00Å |
|  | β = 94.62(4)Å |
|  | γ = 90.00Å |
|  | V = 870.0(7)Å$^3$ |
| Space group | P2$_1$ |
| Molecules/unit cell | Monoclinic 2 |
| Density calculated, g/cm$^3$ | 1.308 |

FIGS. 3, 11, 12, 13 and 14 indicate that Forms I–V differ in their rotational conformation at the methylamino and dichlorophenyl positions. Forms III and IV are similar rotationally but differ in their space groups. Using the absolute configurations, crystal packing diagrams were constructed and crystal densities calculated. As shown in Table 2, the density of Form I is 1.354g/cc, the density of Form II is 1.314g/cc, the density of Form III is 1.313g/cc, the density Form IV gives a density of 1.349g/cc, and the density of Form V is 1.308g/cc. This result supports Form I as the thermodynamically stable form at room temperature since the most dense crystal at a given temperature is considered to be the most thermodynamically stable. (See J. Haleblian and W. McCrione, J. Pharm. Sci., 58(8), 911 (1969).)

Forms I–IV also give distinctive X-ray powder diffraction patterns. The X-ray powder diffraction patterns of Forms I–IV are depicted, respectively, in FIGS. 1, 8, 9 and 10. Each form has diffractions at unique values of 2 θ that are diagnostic:

Form I 7.1, 12.7, 14.1, 15.3, 15.7, 21.2 23.4 and 26.3
Form II 5.4, 10.8, 14.6, 16.3, 18.1, 19.0, 20.3, 21.8, 24.4 and 27.3
Form III 14.3, 15.5, 17.4 and 19.6
Form IV 15.6, 22.4, 25.4, 28.9, 31.9 and 32.1

The results of a single crystal X-ray analysis are limited to, as the name implies, the one crystal placed in the X-ray beam. Crystallographic data on a large group of crystals provides powder X-ray diffraction. If the powder is a pure crystalline compound a simple powder diagram is obtained. To compare the results of a single crystal analysis and powder X-ray analysis a simple calculation can be done converting the single crystal data into a powder X-ray diagram, SHELXTL Plus (trademark) computer program, Reference Manual by Siemens Analytical X-ray Instrument, Chapter 10, p. 179–181, 1990. This conversion is possible because the single crystal experiment routinely determines the unit cell dimensions, space group, and atomic positions. These parameters provide a basis to calculate a perfect powder pattern. Comparing this calculated powder pattern and the powder pattern experimentally obtained from a large collection of crystals will confirm if the results of the two techniques are the same. This has been done for four polymorphs of sertraline hydrochloride, and the results are graphically displayed in FIGS. 18–21. In each of FIGS. 18 through 21, the lower plot corresponds to the experimentally derived powder X-ray diffraction pattern and the second plot corresponds to the X-ray diffraction derived from the single crystal X-ray data. The peak overlap indicates that the two techniques yield the same results. The primary powder X-ray diffraction peaks provide an unambiguous description of each of four polymorphs of sertraline hydrochloride.

Figure 22:
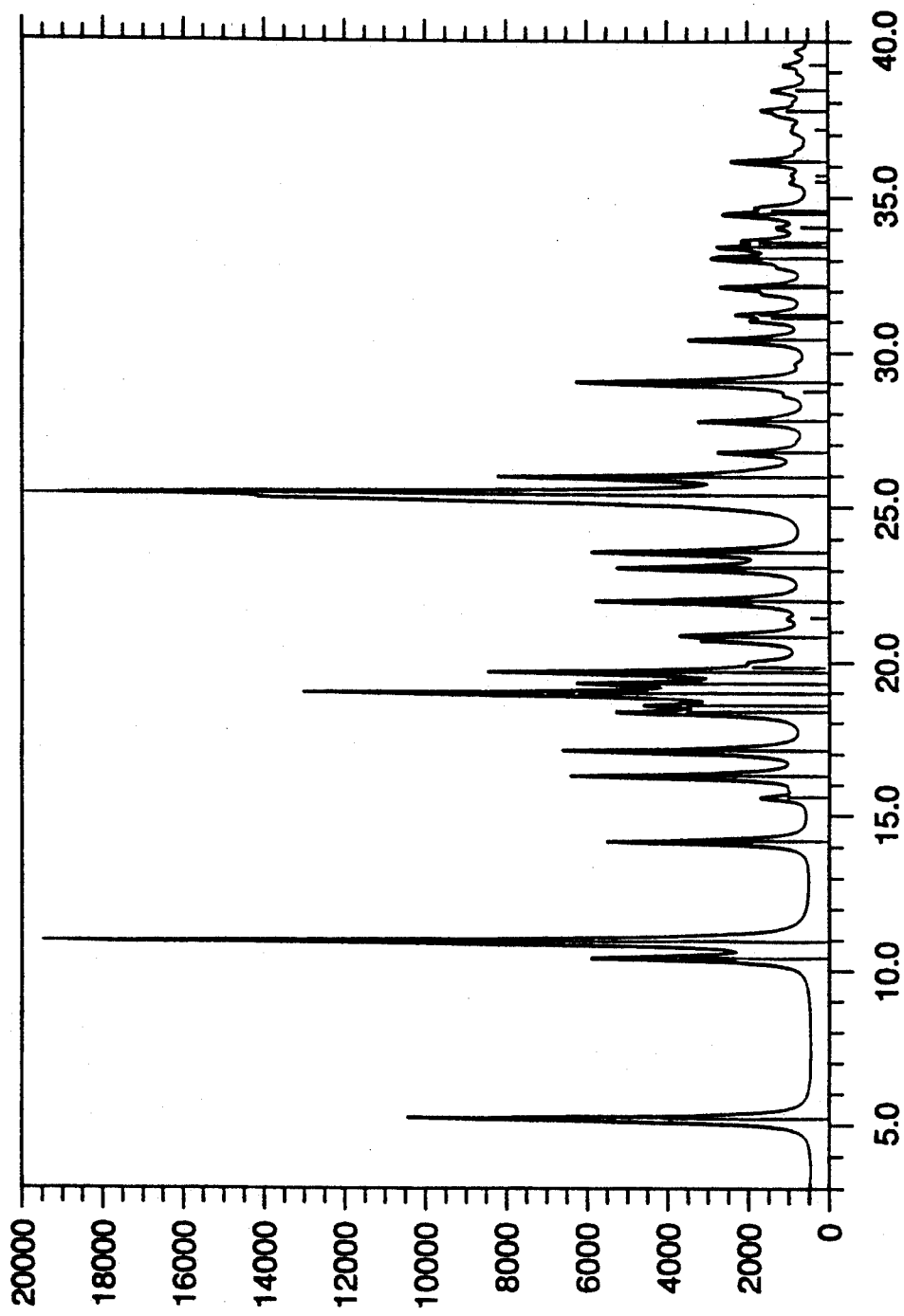
FIG. 22 is a plot of calculated X-ray power diffraction pattern of Form V. (Vertical axis: Intensity (CPS); Horizontal axis: Two Theta (degrees).

This technique of translating single crystal data into a powder diffraction graph has been used to produce a calculated (expected) graph of polymorph V, FIG. 22. The diagnostic powder diffraction at unique values of 2 θ are:

Form V 5.2, 10.4, 10.9, 14.2, 16.3, 17.2, 20.1, 25.3, 25.9 and 29.1.

The powder X-ray diffraction values for each of the polymorphs of sertraline hydrochloride provide a qualitative test for comparison against uncharacterized crystals.

Forms I–IV have been examined by infrared absorption spectroscopy, X-ray powder diffraction, single crystal X-ray, differential scanning calorimetry (DSC), hot stage optical microscopy, and aqueous solubility studies. Form V has been examined by single crystal X-ray.

Form I is the thermodynamically most stable polymorph at room temperature, and would therefore be the most useful active ingredient of a commercial pharmaceutical product.

The infrared absorption spectra of Forms I, II, III, and IV in potassium bromide are different from one another. They are depicted, respectively, in FIGS. 2, 5, 6, and 7. A qualitative comparison of such spectra reveals the following differences:

a. Forms II, III, and IV exhibit absorption bands of significantly higher relative intensity than Form I at approximately 740 to 750cm$^{-1}$ and 1075 to 1085cm$^{-1}$.

b. Forms II, III, and IV exhibit major peaks at approximately 780cm$^{-1}$. Form I exhibits a major peak at approximately 790cm$^{-1}$, with only a shoulder at about 780 cm$^{-1}$.

c. Forms II, III, and IV exhibit absorption bands at approximately 870 and 520 to 540cm$^{-1}$, while no absorption is observed for Form I at these wavelengths.

d. Form II exhibits a strong absorption band and Forms III and IV exhibit a weak absorption band at about 640cm$^{-1}$, while Form I exhibits a barely detectable absorption at that wavelength.

e. Forms II, III and IV exhibit different wavelengths and relative intensities of the absorption bands in the region of 800 to 850cm$^{-1}$ than does Form I.

The differential scanning calorimetry (DSC) thermograms for Forms I-IV are shown, respectively, in FIGS. 4, 15, 16 and 17. The thermograms may be interpreted as follows.

Figure 4:
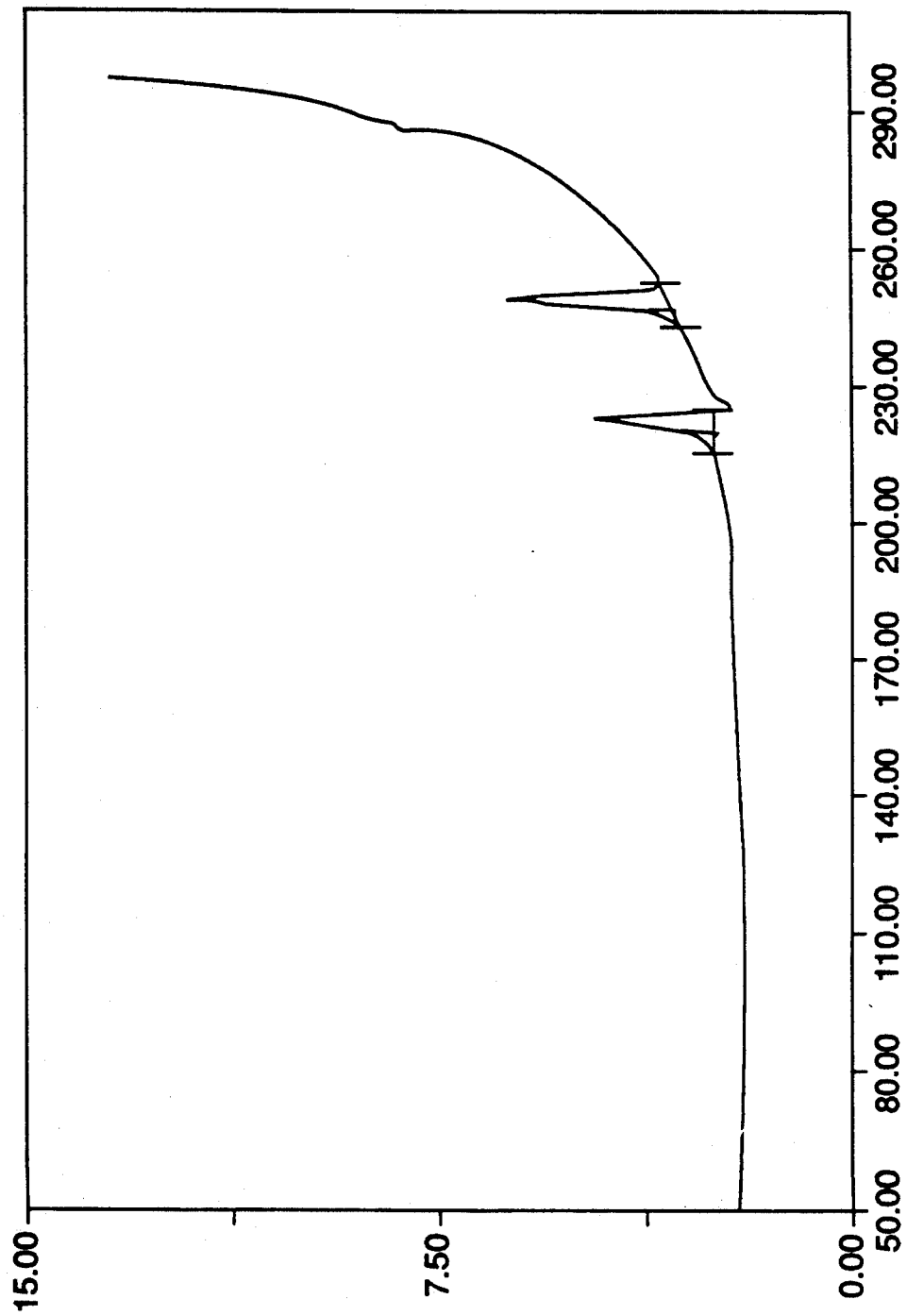
FIG. 4 is a characteristic differential scanning calorimetry thermogram of Form I. (On Perkin Elmer: Thermal Analysis. 20°/min. scan rate. Vertical axis: mcal/sec; Horizontal axis: Temperature (°C.)).
Figure 5:
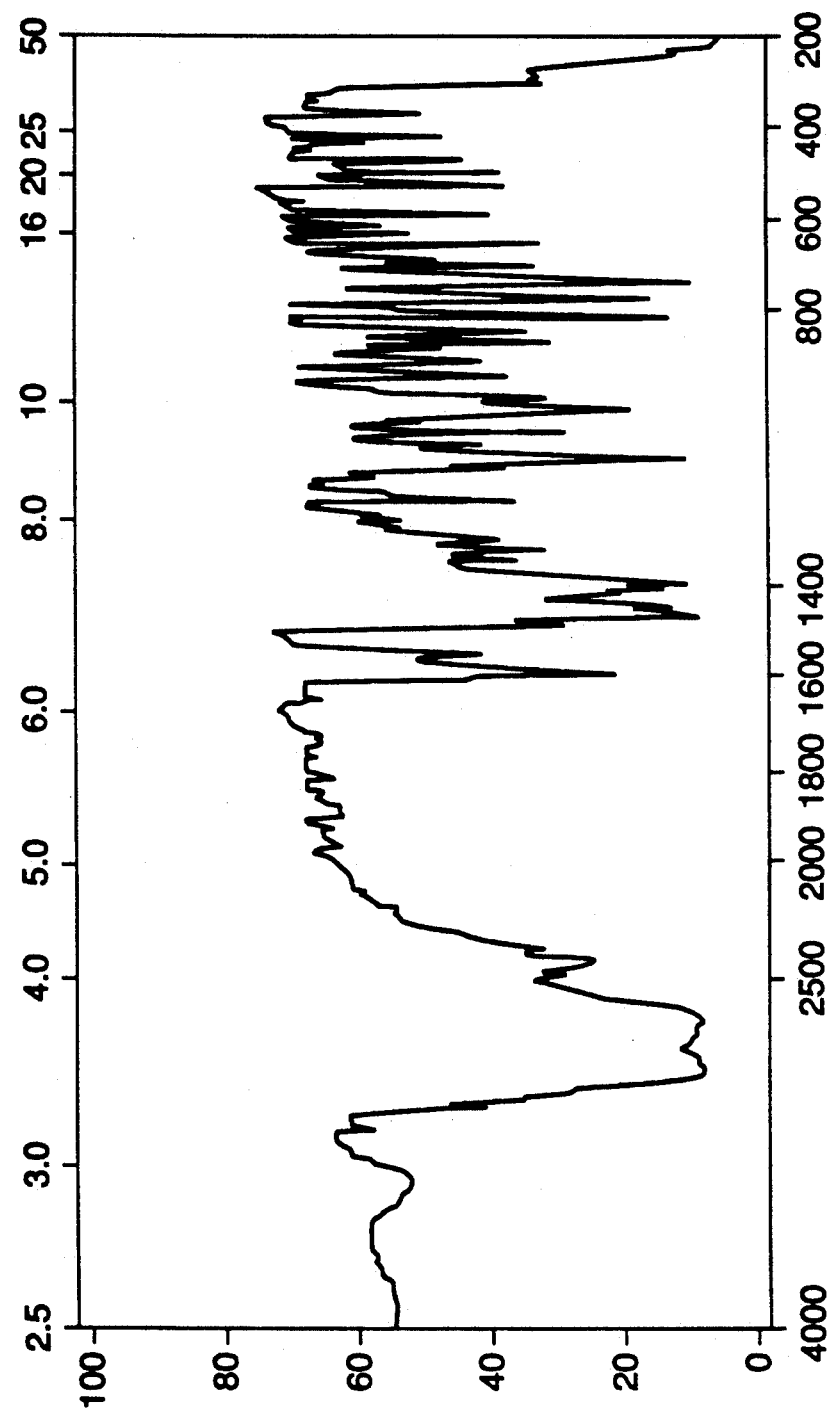
FIG. 5 is a characteristic infrared absorption spectrum in potassium bromide of Form II. (Vertical axis: Transmission (%); Upper horizontal axis: Wavelength (micrometers); Lower horizontal axis: (Wavenumber ($c^{-1}$)).
Figure 6:
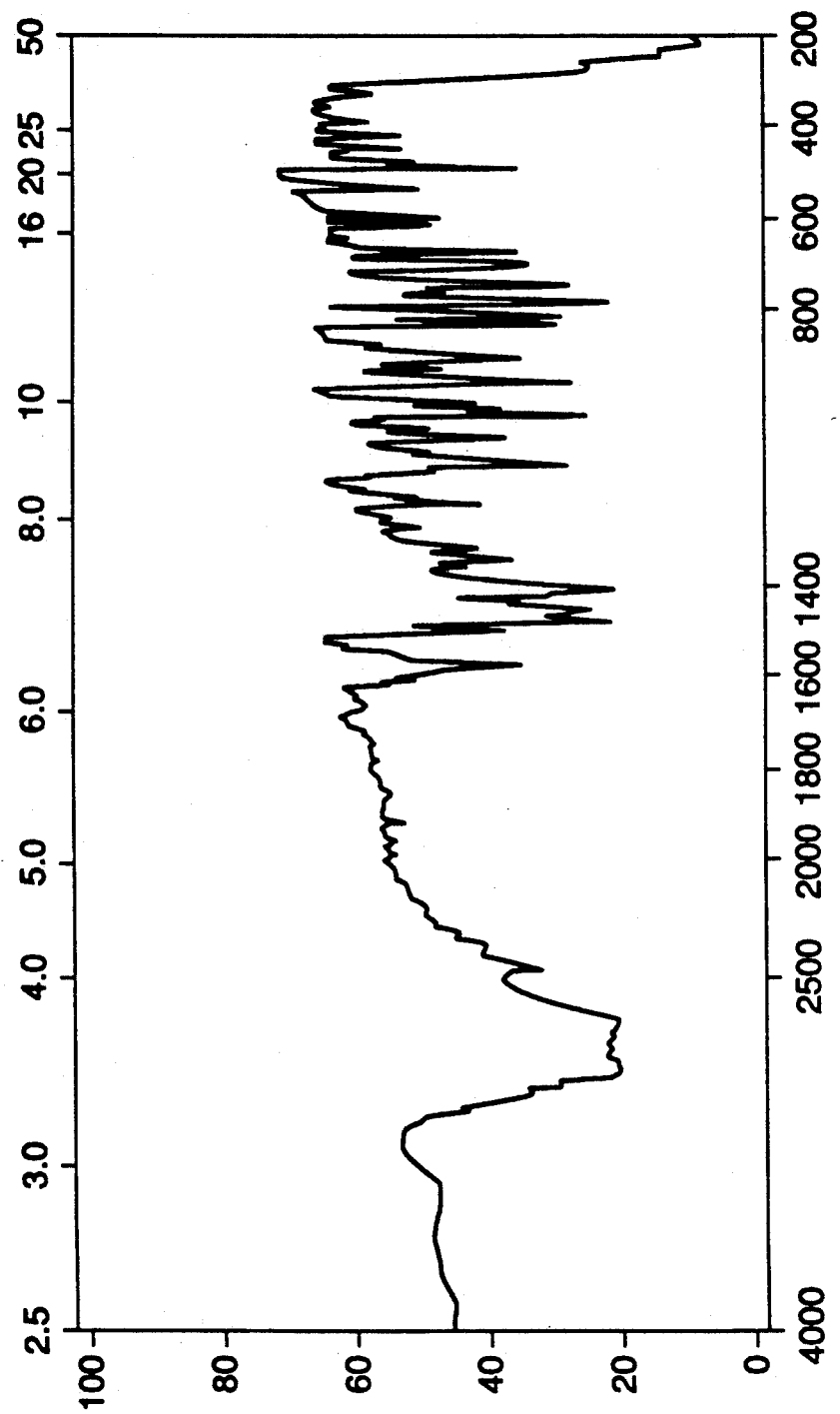
FIG. 6 is a characteristic infrared absorption spectrum in potassium bromide of Form IV. (Vertical axis: Transmission (%); Upper horizontal axis: Wavelength (micrometers); Lower horizontal axis: (Wavenumber ($cm^{-1}$)).
Figure 7:
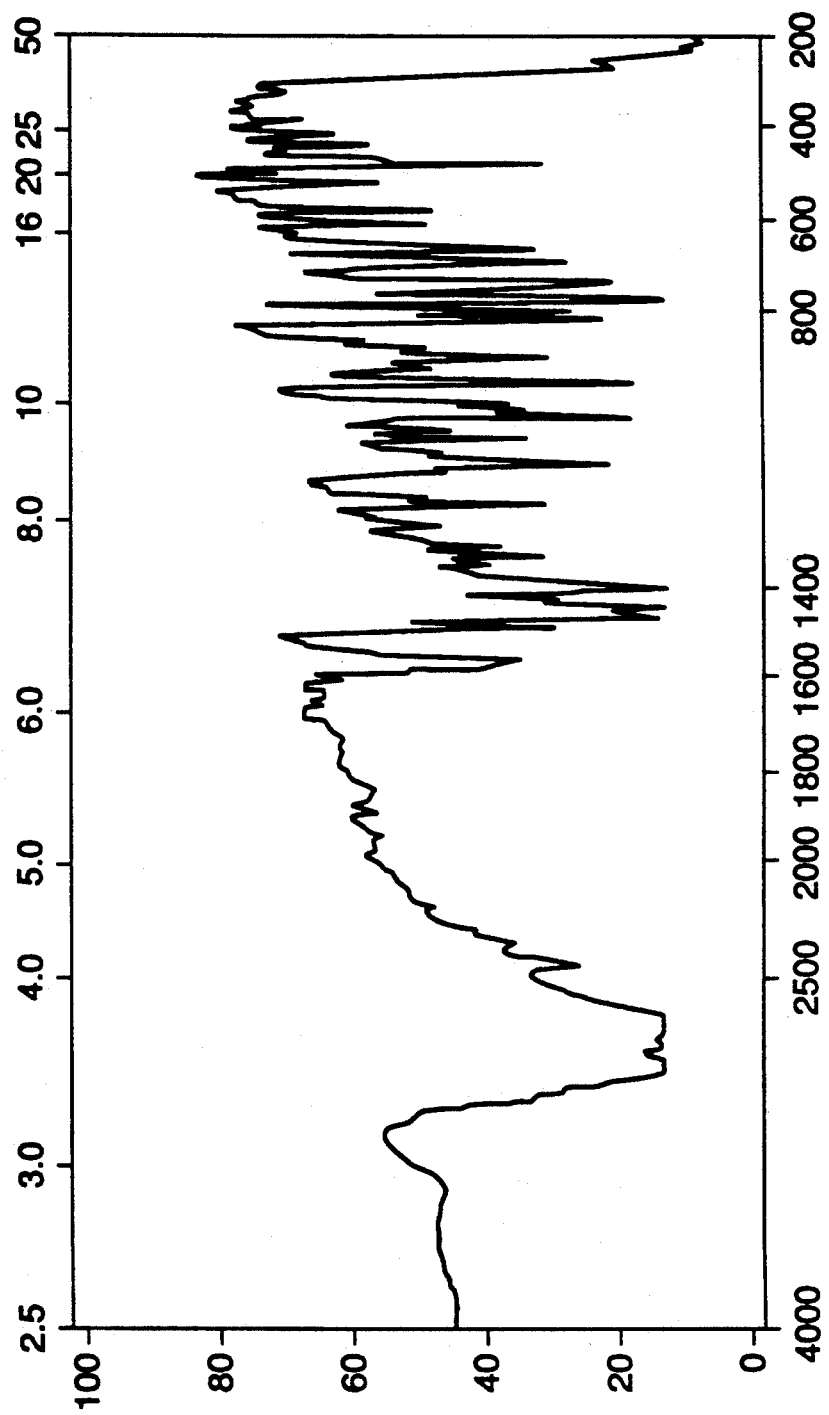
FIG. 7 is a characteristic infrared absorption spectrum in potassium bromide of Form III. (Vertical axis: Transmission (%); Upper horizontal axis: Wavelength (micrometers); Lower horizontal axis: (Wavenumber ($cm^{-1}$)).
Figure 8:
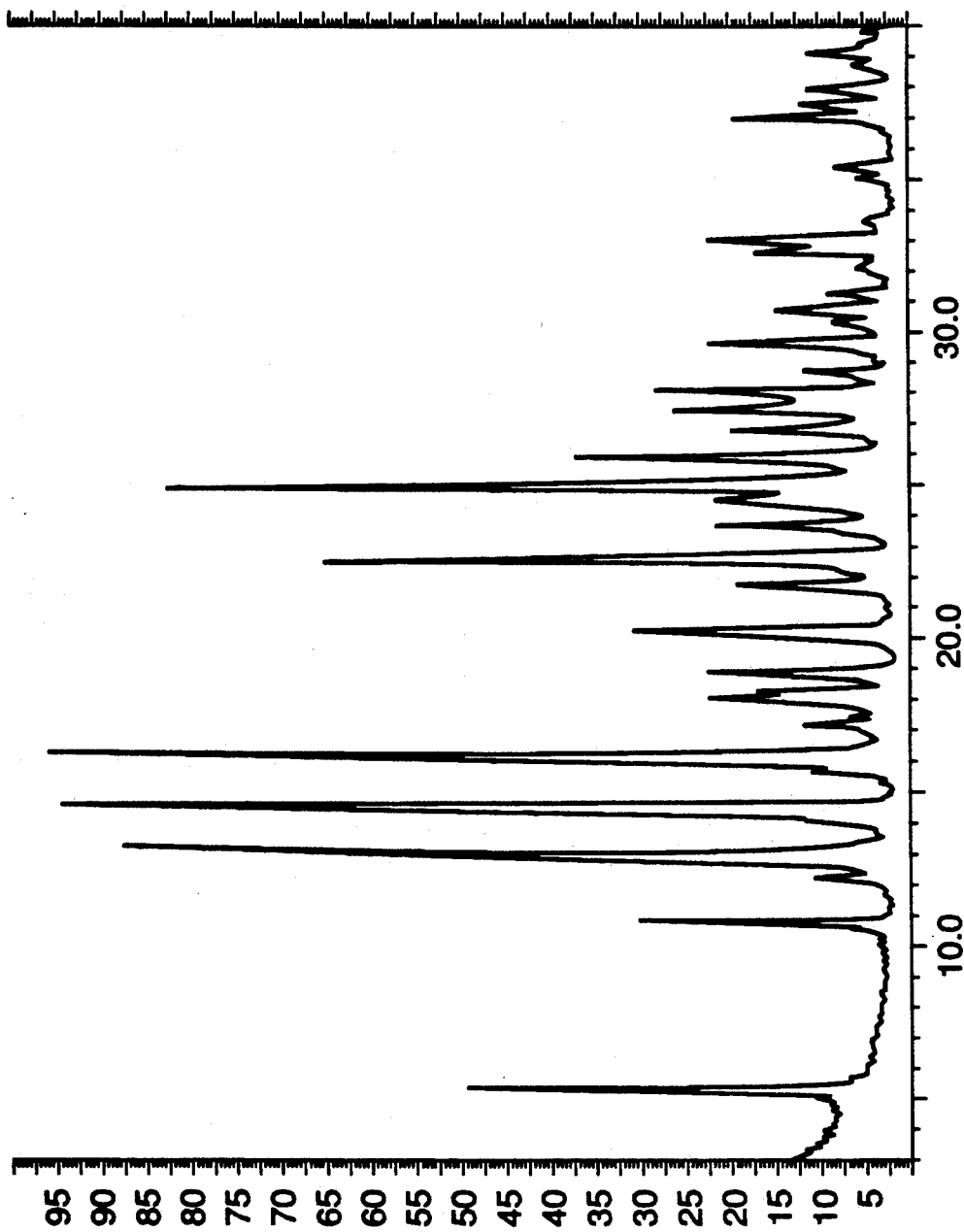
FIG. 8 is a characteristic X-ray powder diffraction pattern for Form II. (Vertical axis: Intensity (CPS); Horizontal axis: Two Theta (degrees)).
Figure 9:
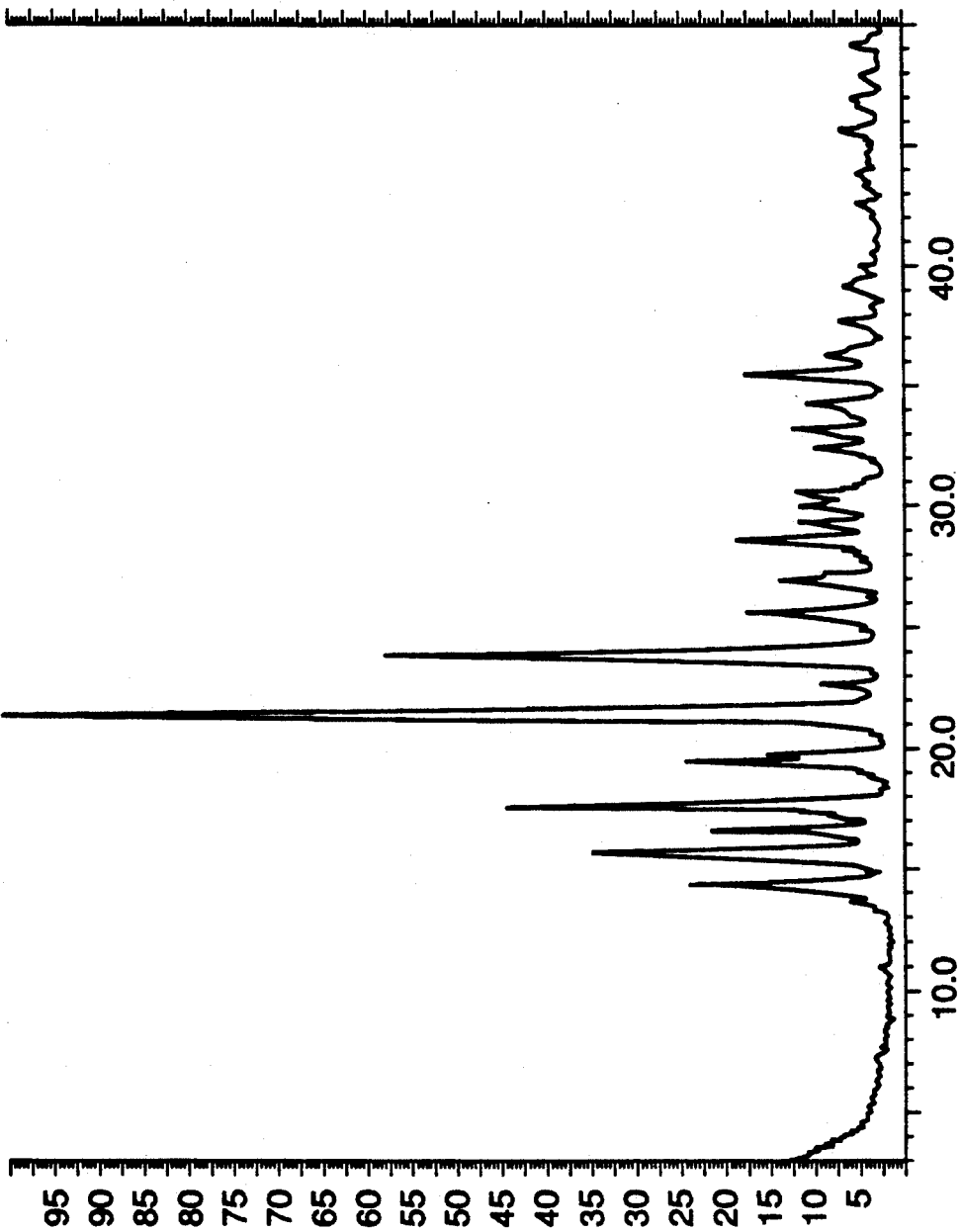
FIG. 9 is a characteristic X-ray powder diffraction pattern for Form III. (Vertical axis: Intensity (CPS); Horizontal axis: Two Theta (degrees)).
Figure 10:
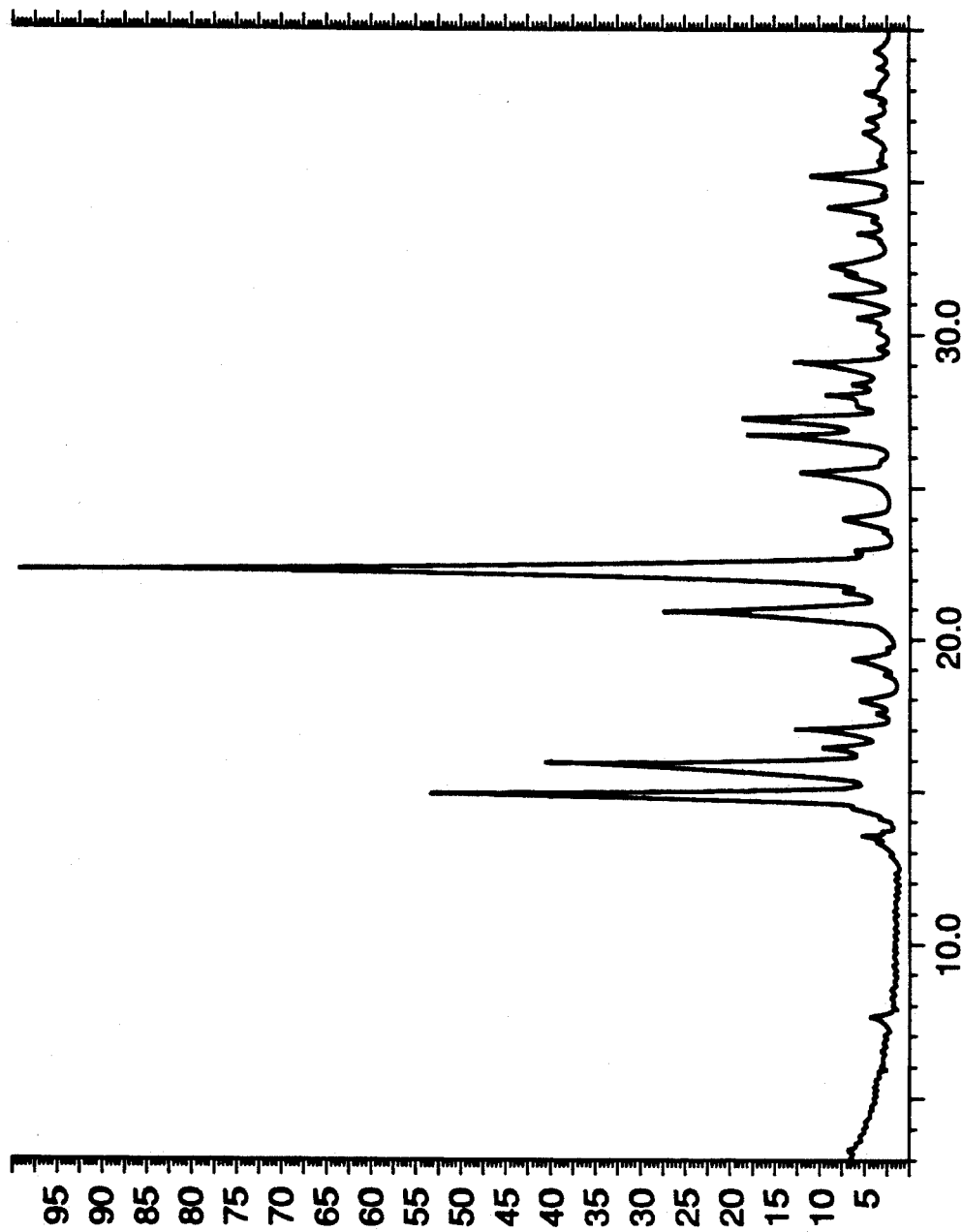
FIG. 10 is a characteristic X-ray powder diffraction pattern for Form IV. (Vertical axis: Intensity (CPS); Horizontal axis: Two Theta (degrees)).
Figure 11:
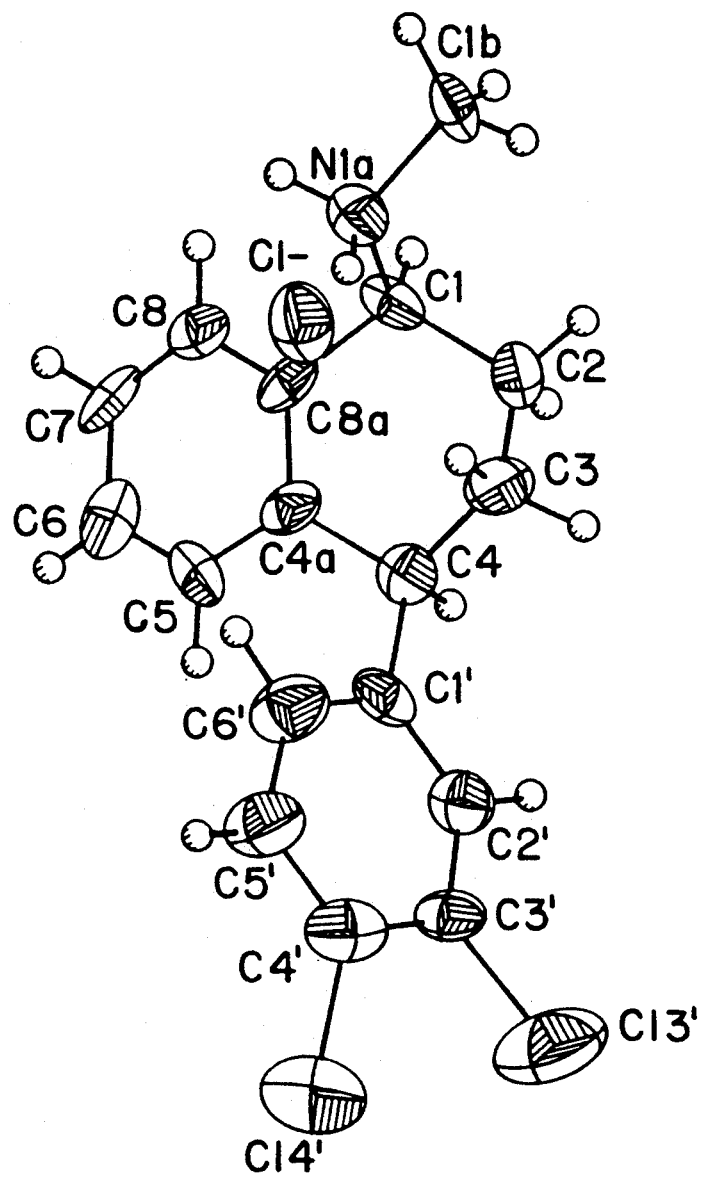
FIG. 11 depicts the absolute configuration of Form II as derived from single crystal X-ray crystallography. (Atomic coordinates).
Figure 12:
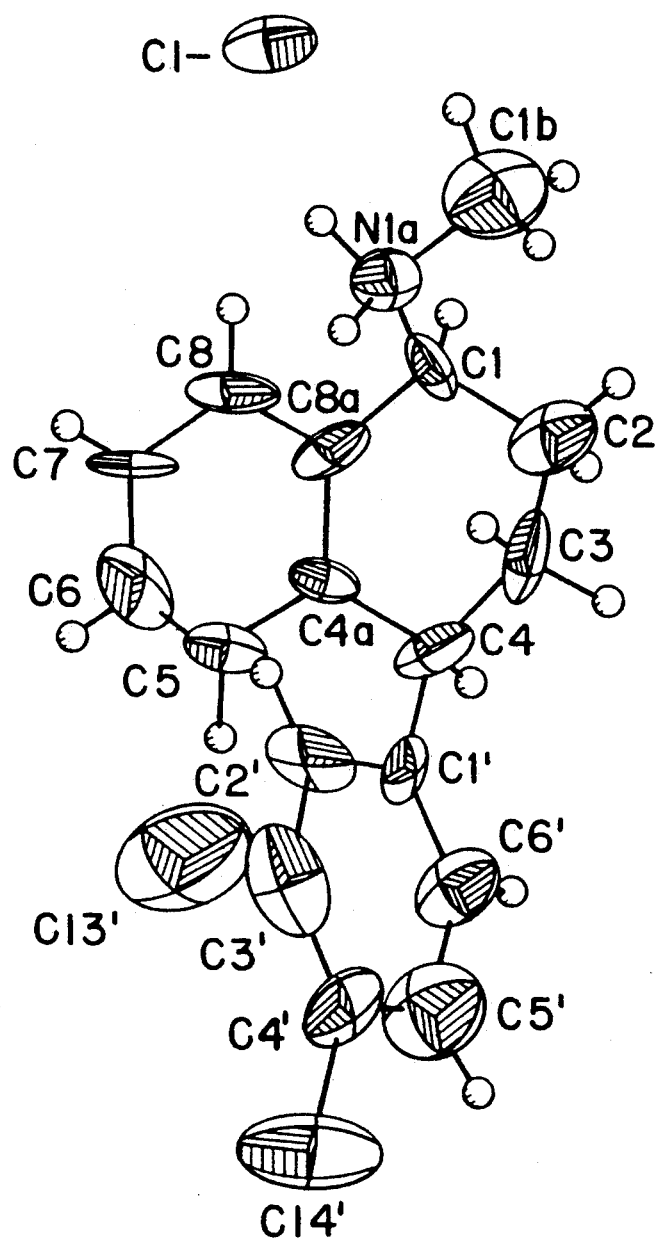
FIG. 12 depicts the absolute configuration of Form III as derived from single crystal X-ray crystallography. (Atomic coordinates).
Figure 13:
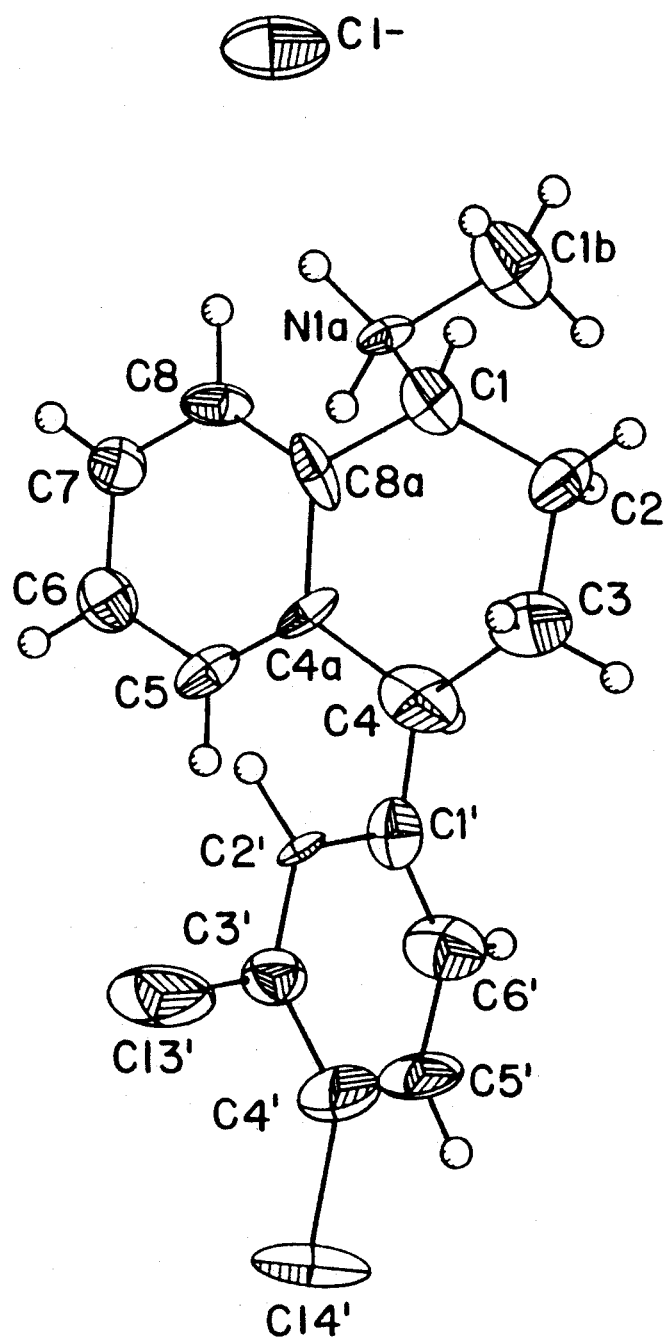
FIG. 13 depicts the absolute configuration of Form IV as derived from single crystal X-ray crystallography. (Atomic coordinates).
Figure 14:
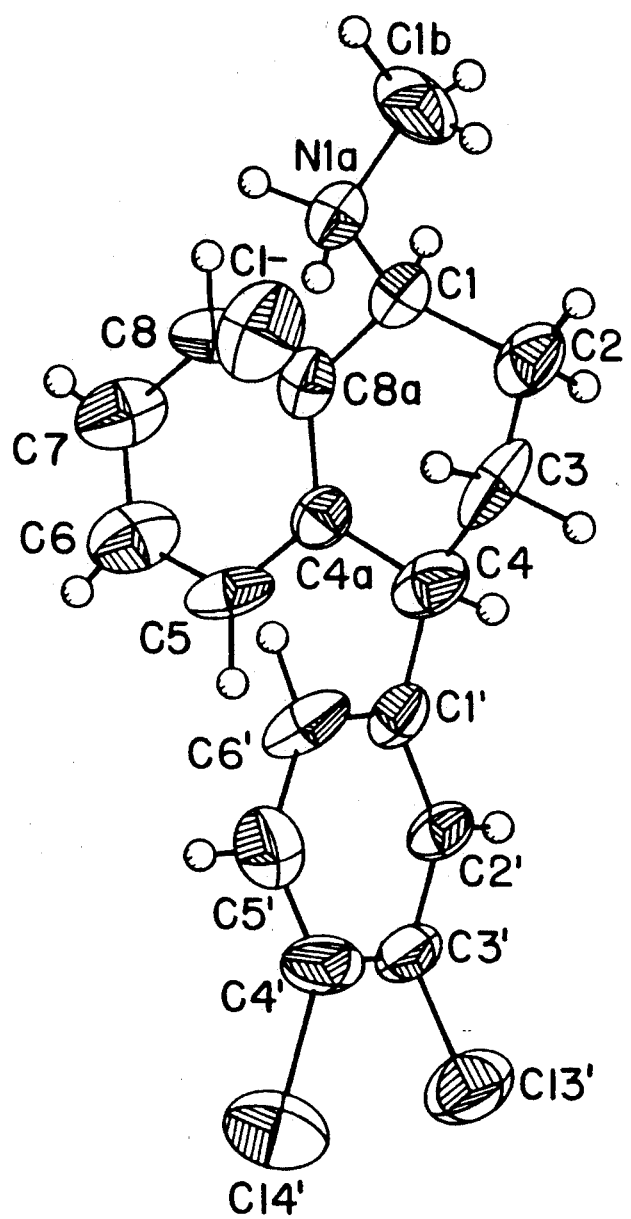
FIG. 14 depicts the absolute configuration of Form V as derived from single crystal X-ray crystallography. (Atomic coordinates).

Referring to FIG. 4, Form I exhibits an endotherm with an onset temperature of about 219° C. resulting from the melting of Form I. An exotherm immediately following the melting endotherm of Form I appears at about 225° C. caused by partial crystallization of the melt to give Form III. Another endotherm appears with an onset at about 246° C. resulting from the melting of Form III. Rapid thermal decomposition takes over after the final melt of Form III causing the baseline to increase rapidly and become erratic in appearance. On rare occasions, the DSC of Form I shows only a single melting endotherm with an onset temperature of about 219° C. This can occur when the sample does not have sufficient time or seed to recrystallize as Form III prior to reaching the Form III melting temperature.

Figure 15:
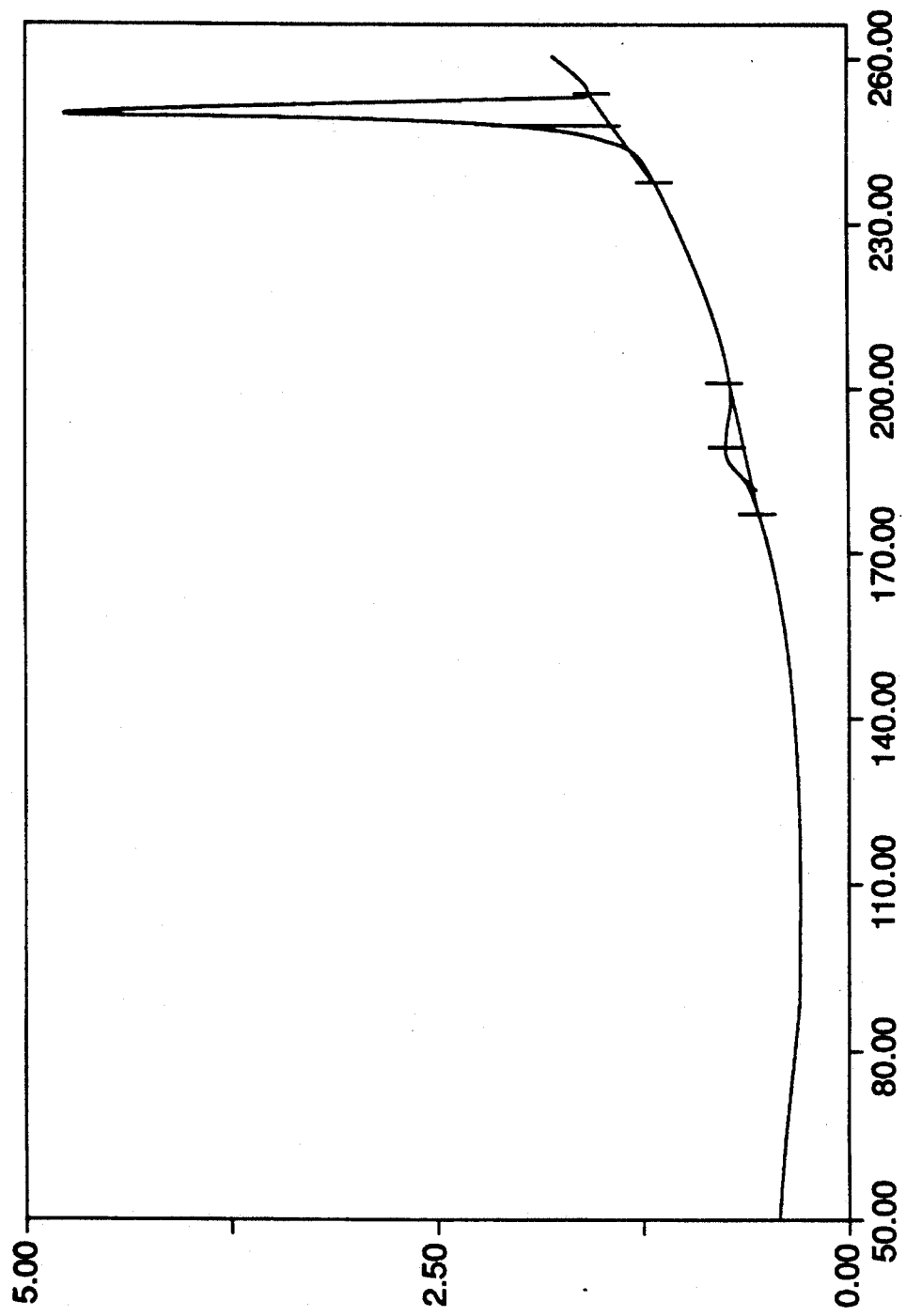
FIG. 15 is a characteristic differential scanning calorimetry thermogram of Form II. (On Perkin Elmer: Thermal Analysis. 20°/min. scan rate. Vertical axis: mcal/sec; Horizontal axis: Temperature (°C.)).
Figure 17:
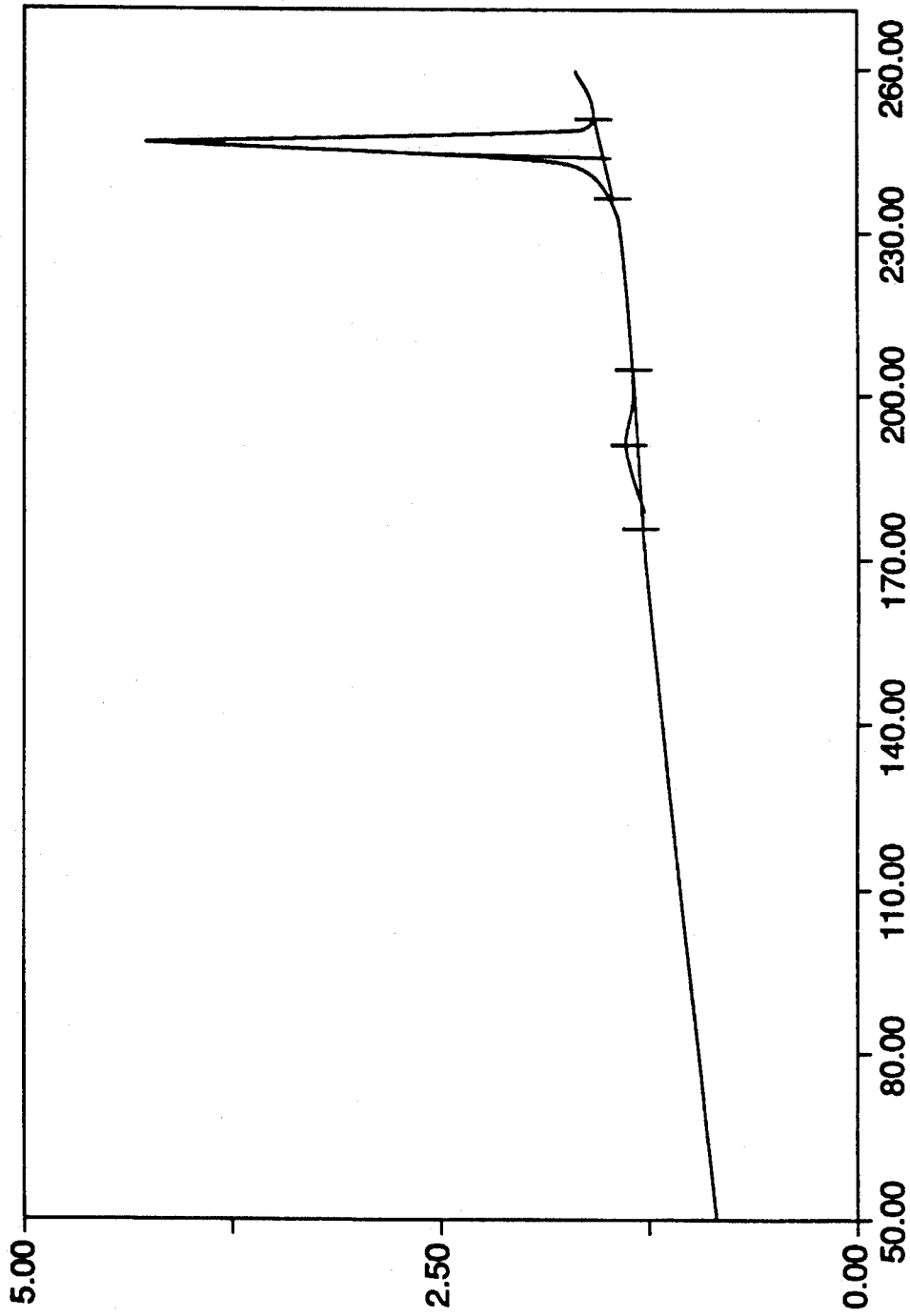
FIG. 17 is a characteristic differential scanning calorimetry thermogram of Form IV. (On Perkin Elmer: Thermal Analysis. 20°/min. scan rate. Vertical axis mcal/sec; Horizontal axis: Temperature (°C.)).
Figure 18:
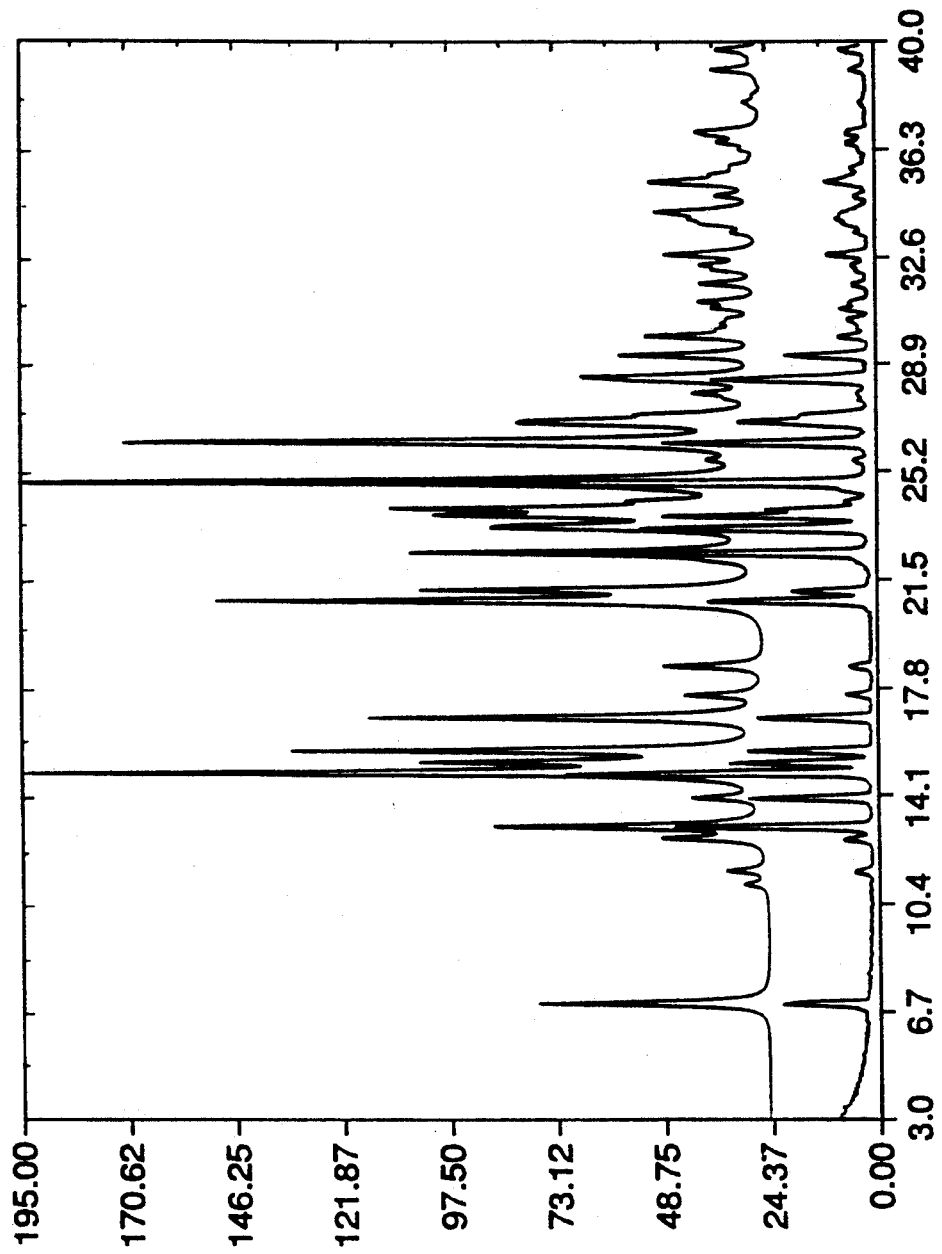
FIG. 18 is a plot of calculated versus experimental X-ray power diffraction patterns of Form I. (Vertical axis: Intensity (CPS); Horizontal axis: Two Theta (degrees). Upper plot calculated powder pattern; Lower plot experimental powder pattern).
Figure 19:
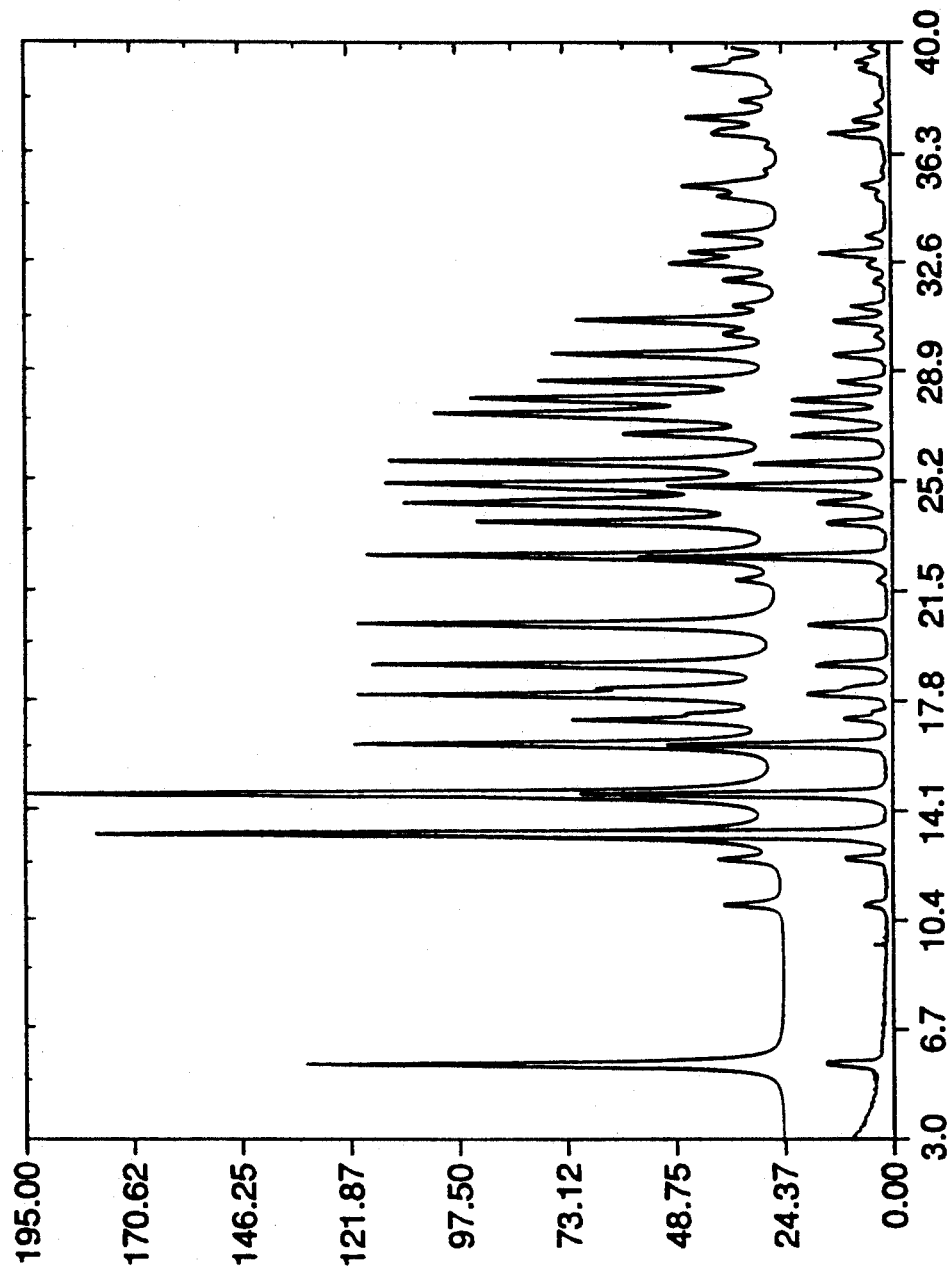
FIG. 19 is a plot of calculated versus experimental X-ray power diffraction patterns of Form II. (Vertical axis: Intensity (CPS); Horizontal axis: Two Theta (degrees). Upper plot calculated powder pattern; Lower plot experimental powder pattern).
Figure 20:
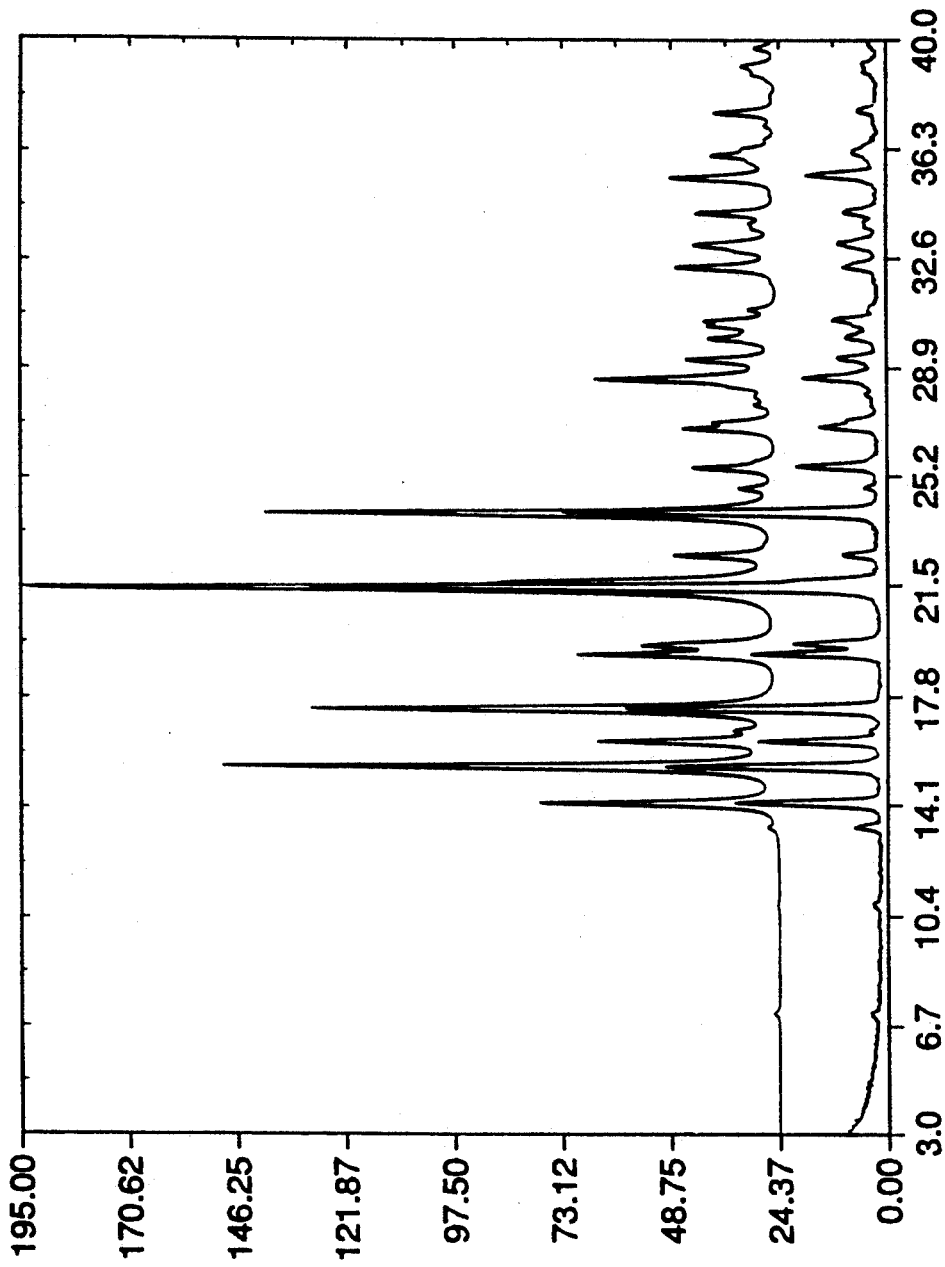
FIG. 20 is a plot of calculated versus experimental X-ray power diffraction patterns of Form III. (Vertical axis: Intensity (CPS); Horizontal axis: Two Theta (degrees). Upper plot calculated powder pattern; Lower plot experimental powder pattern).
Figure 21:
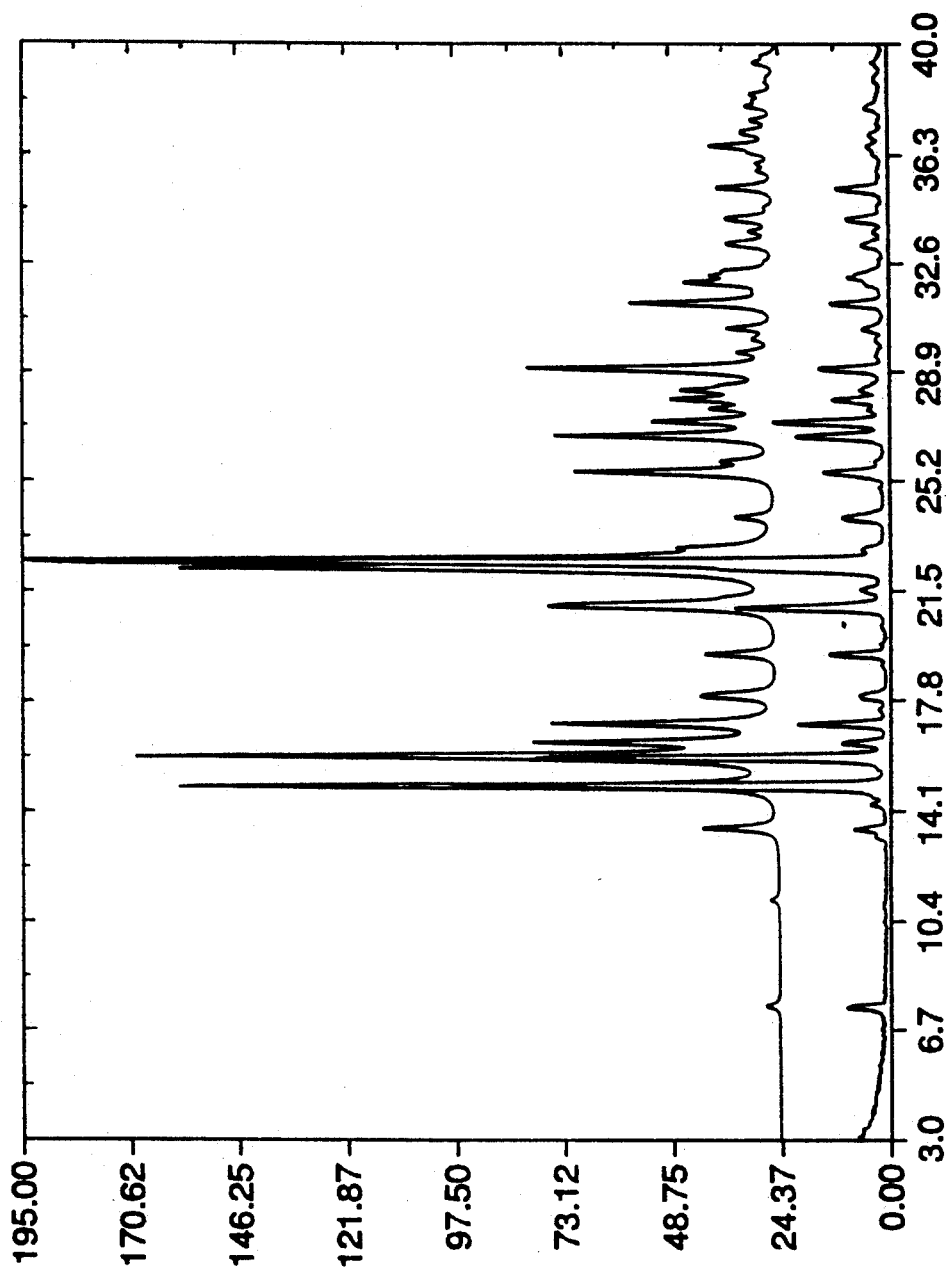
FIG. 21 is a plot of calculated versus experimental X-ray power diffraction patterns of Form IV. (Vertical axis: Intensity (CPS); Horizontal axis: Two Theta (degrees). Upper plot calculated powder pattern; Lower plot experimental powder pattern).

In the thermograms obtained for Forms II and IV, referring to FIGS. 15 and 17, a very small endotherm may be observed with an onset temperature at about 180° C., which corresponds to a solid-solid transition to Form III. This event is followed by melting of Form III at about 246° C.

Figure 16:
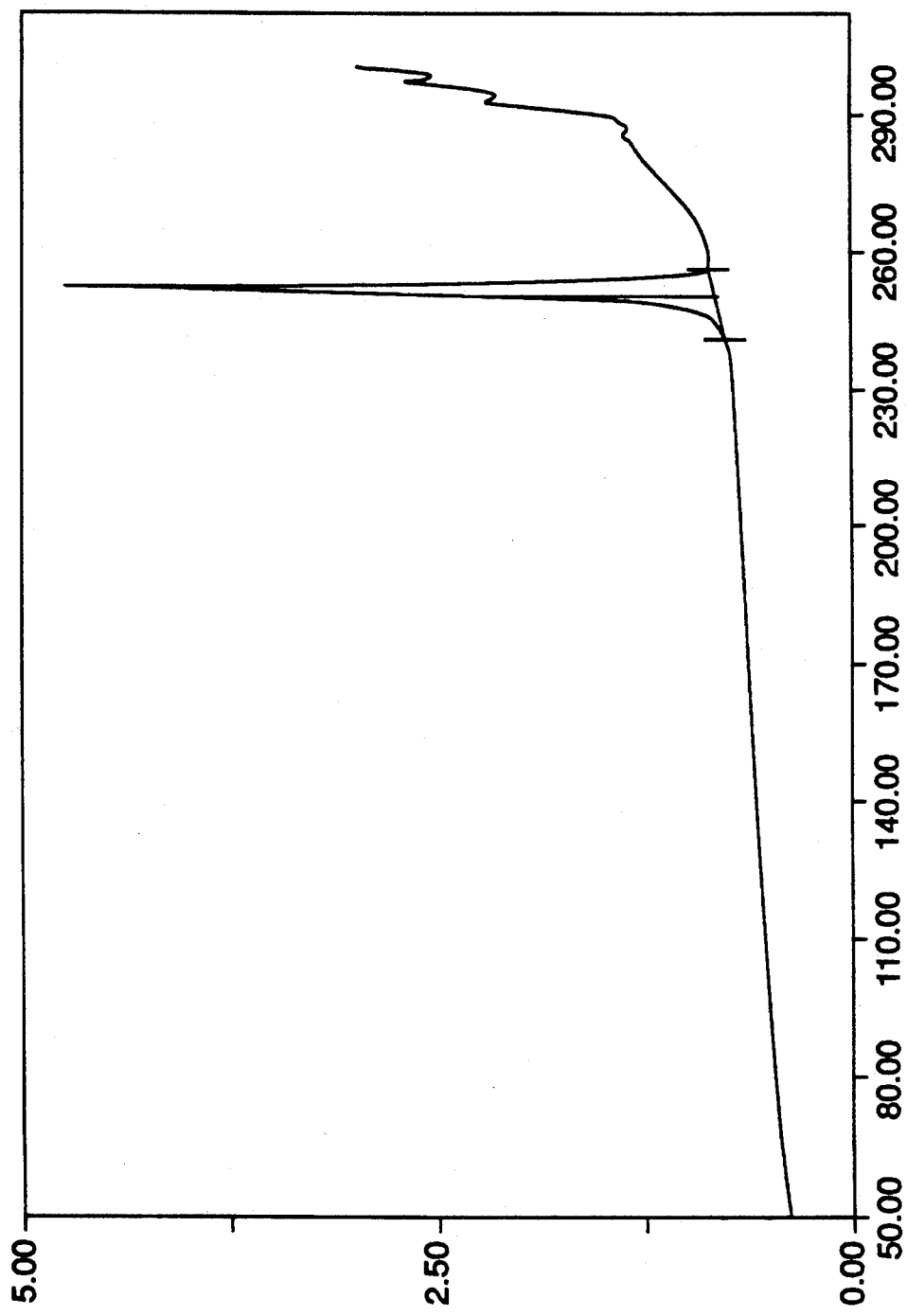
FIG. 16 in a characteristic differential scanning calorimetry thermogram of Form III. (On Perkin Elmer: Thermal Analysis. 20°/min. scan rate. Vertical axis: mcal/sec; Horizontal axis: Temperature (°C.)).

FIG. 16 represents the thermogram obtained for Form III and is characterized by a single endotherm at about 246° C. Above the melting temperature of 246° C., thermal decomposition increases rapidly.

The thermal events discussed above demonstrate that Form III undergoes only a single melting process at 246° C. followed by increased thermal decomposition after the melt has occurred. Thermogravimetry and hot stage optical microscopy reveal that all four forms undergo slight decomposition and sublimation at temperatures above about 160° C.

Prolonged heating studies on the Form I to Form III conversion in the solid state have shown that below 160° C. Form I is the preferred polymorph. Above 180° C. Form I converts to Form III in the solid state. This conversion takes place at varying rates, as shown by DSC experiments, depending on sample characteristics such as particle size, previous handling, or the presence of Form III seed. Thus, in some instances the first endotherm in Form I may exhibit a smaller endotherm with a lower onset temperature as a result of the solid state conversion of Form I to Form III during heating. The solid state conversion of Form I to Form II is a very low energy transition and fails to give a reliably detectable DSC event. A sample of Form I spiked with 3% of Form III exhibits an endotherm for the solid state transition and the absence of the Form I melting endotherm. The Form II endotherm appears at the expected temperature of about 246° C. Under the conditions of this DSC experiment, the solid state transition is fast enough to cause complete conversion to Form III before the Form I melting temperature is reached. In two other samples of Form I spiked with 5% of Form II or 5% of Form IV, similar thermograms were observed.

In a related experiment, small amounts of each of Forms I, II, and IV were heated to 185° C. for 15 minutes. The infrared spectra of each sample confirmed that each had converted to Form III.

Hot stage optical microscopy data for Form I is consistent with observed DSC behavior. When heated on a hot stage microscopic observation of a sample of Form I shows that at about 150° to 180° C., the sample begins to move about and appears to "pop". This may be caused by the onset of decomposition, solvent release, or sublimation. Partial melting may be observed at about 210° to 220° C. with formation of some new crystals (Form III) as the temperature is raised to about 235° C. (In some instances, a solid-solid transition to Form III is observed at temperatures above about 180° C.). At about 245° to 250° C., the newly formed crystals melt completely. The melt solidifies very slowly upon cooling and usually remains as a yellowish glass. This suggests that significant decomposition has taken place.

In mixtures of Form III in Form I, the first melt at 210° to 220° C. does not cause all of the sample to liquefy; a small number of crystals may remain and increase in size as Form III crystallizes around them. Holding the temperature at about 235° C. permits the melt to recrystallize to Form III. Cooling this melt to room temperature and subsequent reheating does not exhibit the Form I melt at 210° to 220° C. This suggests that the conversion to Form III is not rapidly reversible under these conditions.

Microscopic observation of Forms II or IV on the hot stage shows an apparent solid/solid transition at about 180° C. without evidence of melting. Continued heating gives a complete melt at about 245° C. The temperature region of 180° to 230° C. appears also to cause decomposition and sublimation.

Microscopic observations of Form III reveals sample movement similar to Form I at about 160° C., followed by melting at about 245° to 250° C. No other thermal events are seen. These observations are consistent with DSC behavior.

When samples of Forms I-IV are heated in silicone oil, gas bubbles are observed starting at around 150° to 180° C., suggesting the onset of decomposition. The yellowish color of the melt above 250° C. results from chemical decomposition of the sample. This phenomenon occurs for all of Forms I-IV.

Determination of the melting point of Form I by the capillary method shows the onset of change at about 160° to 180° C. with movement of the sample and a slight color change. (The melting point is defined as the point at which the sample is entirely in the liquid phase). At about 218° C. a partial melt is observed but the sample does not become clear until a temperature of 245° to 250° C. is reached. This is consistent with DSC and hot stage microscopy data.

TABLE 3

Atomic Coordinates (×10) and Isotropic Thermal Parameters ($\text{Å}^2 \times 10^3$)

| | x | y | z | U |
|---|---|---|---|---|
| C(1) | 8349(29) | 7105(18) | 8167(9) | 44(2)* |
| C(2) | 10591(29) | 7572(20) | 8159(11) | 70(2)* |
| C(3) | 10594(30) | 8946(19) | 8299(10) | 62(2)* |
| C(4) | 9862(30) | 9096(18) | 8888(9) | 55(2)* |
| C(4A) | 7911(27) | 8422(16) | 8999(7) | 28(2)* |
| C(5) | 6795(29) | 8662(18) | 9463(8) | 45(2)* |
| C(6) | 5153(30) | 7950(20) | 9602(9) | 64(2)* |
| C(7) | 4424(30) | 6998(15) | 9303(7) | 41(2)* |
| C(8) | 5558(30) | 6722(17) | 8824(9) | 57(2)* |
| C(8A) | 7357(28) | 7412(17) | 8682(9) | 40(2)* |
| C(1') | 9846(28) | 10518(17) | 8992(8) | 37(2)* |
| C(2') | 8210(31) | 11245(16) | 8781(9) | 53(2)* |
| C(3') | 8416(32) | 12507(19) | 8922(9) | 62(2)* |
| C(4') | 9864(30) | 13010(19) | 9261(11) | 66(2)* |
| C(5') | 11396(35) | 12295(18) | 9427(12) | 108(2)* |
| C(6') | 11317(31) | 11029(18) | 9322(10) | 76(2)* |
| N(1A) | 7072(25) | 7449(15) | 7683(6) | 47(2)* |
| C(1B) | 8149(32) | 7295(21) | 7147(9) | 79(2)* |
| Cl(3') | 6586(17) | 13408(7) | 8570(5) | 152(2)* |
| Cl(4') | 9811(16) | 14605(6) | 9312(3) | 116(2)* |
| Cl- | 4145(11) | 5217(5) | 7479(2) | 63(2) |

*Equivalent isotropic U defined as one third of the trace of the orthogonalized $U_{ij}$ tensor.

TABLE 4

Bond Lengths (Å)

| | | | |
|---|---|---|---|
| C(1)-C(2) | 1.530(27) | C(1)-C(8A) | 1.468(30) |
| C(1)-N(1A) | 1.502(26) | C(2)-C(3) | 1.530(30) |
| C(3)-C(4) | 1.543(32) | C(4)-C(4A) | 1.480(26) |
| C(4)-C(1') | 1.563(27) | C(4A)-C(5) | 1.382(27) |
| C(4A)-C(8A) | 1.394(26) | C(5)-C(6) | 1.354(28) |
| C(6)-C(7) | 1.355(27) | C(7)-C(8) | 1.428(28) |
| C(8)-C(8A) | 1.423(27) | C(1')-C(2') | 1.415(27) |
| C(1')-C(6') | 1.369(29) | C(2')-C(3') | 1.418(27) |
| C(3')-C(4') | 1.369(31) | C(3')-Cl(3') | 1.762(23) |
| C(4')-C(5') | 1.320(30) | C(4')-Cl(4') | 1.734(22) |
| C(5')-C(6') | 1.398(28) | N(1A)-C(1B) | 1.511(26) |

TABLE 5

Bond Angles (°)

| | | | |
|---|---|---|---|
| C(2)-C(1)-C(8A) | 110.3(18) | C(2)-C(1)-N(1A) | 115.1(18) |
| C(8A)-C(1)-N(1A) | 113.7(15) | C(1)-C(2)-C(3) | 108.7(16) |
| C(2)-C(3)-C(4) | 108.5(18) | C(3)-C(4)-C(4A) | 112.6(17) |
| C(3)-C(4)-C(1') | 105.2(16) | C(4A)-C(4)-C(1') | 116.8(16) |
| C(4)-C(4A)-C(5) | 120.3(17) | C(4)-C(4A)-C(8A) | 120.0(17) |
| C(5)-C(4A)-C(8A) | 119.0(17) | C(4A)-C(5)-C(6) | 120.7(18) |
| C(5)-C(6)-C(7) | 124.5(19) | C(6)-C(7)-C(8) | 116.0(17) |
| C(7)-C(8)-C(8A) | 120.8(18) | C(1)-C(8A)-C(4A) | 123.9(17) |
| C(1)-C(8A)-C(8) | 116.7(17) | C(4A)-C(8A)-C(8) | 118.8(18) |
| C(4)-C(1')-C(2') | 119.5(16) | C(4)-C(1')-C(6') | 119.6(17) |
| C(2')-C(1')-C(6') | 120.7(17) | C(1')-C(2')-C(3') | 112.2(18) |
| C(2')-C(3')-C(4') | 126.7(20) | C(2')-C(3')-Cl(3') | 110.5(16) |
| C(4')-C(3')-Cl(3') | 122.7(16) | C(3')-C(4')-C(5') | 117.9(20) |
| C(3')-C(4')-Cl(4') | 115.4(16) | C(5')-C(4')-Cl(4') | 125.2(17) |
| C(4')-C(5')-C(6') | 119.4(21) | C(1')-C(6')-C(5') | 122.3(20) |
| C(1)-N(1A)-C(1B) | 115.2(15) | | |

TABLE 6

Anisotropic Thermal Parameters ($\text{Å}^2 \times 10^3$)

| | $U_{11}$ | $U_{22}$ | $U_{33}$ | $U_{23}$ | $U_{13}$ | $U_{12}$ |
|---|---|---|---|---|---|---|
| C(1) | 50(4) | 32(4) | 49(4) | −14(4) | 23(4) | 7(4) |
| C(2) | 62(4) | 71(4) | 76(4) | 1(4) | −30(4) | 10(4) |
| C(3) | 22(4) | 60(4) | 104(4) | 5(4) | 8(4) | 5(4) |
| C(4) | 49(4) | 48(4) | 67(4) | −10(4) | −22(4) | −16(4) |
| C(4A) | 32(4) | 25(4) | 28(4) | 1(4) | −18(4) | 8(4) |
| C(5) | 62(4) | 32(4) | 41(4) | −9(4) | −1(4) | −9(4) |
| C(6) | 86(4) | 72(4) | 34(4) | 4(4) | 36(4) | −7(4) |
| C(7) | 78(4) | 19(4) | 27(4) | −6(4) | −6(4) | −31(4) |
| C(8) | 92(4) | 16(4) | 62(4) | −15(4) | −41(4) | 19(4) |
| C(8A) | 35(4) | 20(4) | 64(4) | 3(4) | −18(4) | −9(4) |
| C(1') | 36(4) | 34(4) | 40(4) | 12(4) | 17(4) | −20(4) |
| C(2') | 73(4) | 15(4) | 71(4) | −4(4) | −16(4) | 19(4) |
| C(3') | 70(4) | 45(4) | 69(4) | 34(4) | 12(4) | 40(4) |
| C(4') | 46(4) | 46(4) | 105(4) | −4(4) | 15(4) | −37(4) |
| C(5') | 104(4) | 94(4) | 125(4) | 9(4) | −35(4) | 2(4) |
| C(6') | 68(4) | 52(4) | 98(4) | 7(4) | −43(4) | 9(4) |
| N(1A) | 54(4) | 33(4) | 54(4) | 2(4) | 1(4) | −14(4) |
| C(1B) | 91(4) | 85(4) | 61(4) | 15(4) | −18(4) | −9(4) |
| Cl(3') | 157(4) | 56(3) | 244(4) | −19(4) | −74(4) | 7(4) |
| Cl(4') | 188(4) | 39(3) | 123(3) | −17(3) | −11(4) | −31(3) |
| Cl-. | 89(3) | 38(2) | 61(3) | −11(3) | −17(3) | −14(3) |

TABLE 7

H-Atom Coordinates (×$10^4$) and Isotropic Thermal Parameters ($\text{Å}^2 \times 10^3$)

| | x | y | z | U |
|---|---|---|---|---|
| H(1) | 8427 | 6224 | 8135 | 59 |
| H(2A) | 11184 | 7452 | 7808 | 73 |
| H(2B) | 11390 | 7126 | 8421 | 73 |
| H(3A) | 11975 | 9268 | 8261 | 64 |
| H(3B) | 9672 | 9380 | 8062 | 64 |
| H(4) | 10779 | 8724 | 9145 | 119 |
| H(5) | 7206 | 9334 | 9691 | 70 |
| H(6) | 4446 | 8140 | 9932 | 99 |
| H(7) | 3224 | 6530 | 9408 | 43 |
| H(8) | 5098 | 6064 | 8594 | 45 |
| H(2') | 7094 | 10920 | 8568 | 62 |
| H(5') | 12574 | 12652 | 9606 | 60 |
| H(6') | 12250 | 10468 | 9497 | 85 |
| H(1AA) | 5846 | 6946 | 7683 | 44 |
| H(1AB) | 6685 | 8301 | 7718 | 44 |
| H(1BA) | 9105 | 6617 | 7169 | 67 |
| H(1BB) | 8891 | 8035 | 7057 | 67 |
| H(1BC) | 7135 | 7127 | 6873 | 67 |

The novel crystalline polymorphic Forms I-V may be prepared as described below.

Form I may be formed by crystallizing sertraline hydrochloride in an acidic solution using solvent such as isopropyl alcohol, hexane, ethyl acetate, acetone, methyl isobutyl ketone, glacial acetic acid, and ethyl acetate is the preferred solvent. The crystallization is carried out at a temperature from about 20° to about the solvent reflux temperature, preferably from about 40° to about 60° C.

The metastable Forms II and IV may be formed by the rapid crystallization of sertraline hydrochloride from an organic solvent such as those listed above. However, slow crystallization or granulation of sertraline hydrochloride will produce Form I. Form III may be produced from Forms I, II or IV by heating to temperatures above about 180° C. Granulating either of Forms II, III or IV in isopropyl alcohol, ethyl acetate, hexane or any of the solvents listed above at a temperature from about 40° to about 60° C. causes conversion to Form I.

Form V may be prepared by the sublimation of sertraline hydrochloride at a reduced pressure at a temperature from about 180° to about 190° C.

Sertraline is used as the starting material for the preparation of Forms I-V of sertraline hydrochloride. Sertraline may be prepared as described in U.S. Pat. No. 4,536,518, and particularly, in Example 2 of that patent.

Form I of sertraline hydrochloride, when used to treat depression, obesity, a chemical dependency or an anxiety-related disorder, may be administered either orally or parenterally. It is generally administered in dosages ranging from about 50-200mg per day when used to treat used to treat obsessive-compulsive disorder, from about 25-500mg per day when used to treat other anxiety-related disorders, and from about 0.3-10mg per kg of body weight per day when used to treat depression or obesity. Variations will necessarily occur depending upon the condition of the subject being treated and the particular route of administration chosen. It may be administered either alone or in combination with pharmaceutically acceptable carriers by either of the above routes, and such administration can be carried out in both single and multiple dosages. More particularly, sertraline, or a pharmaceutically acceptable salt thereof, may be administered in a wide variety of different dosage forms, i.e., it may be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, sertraline, or a pharmaceutically acceptable salt thereof, when used to treat an anxiety-related disorder, is present in such dosage forms at concentration levels ranging from about 0.5% to about 90% by weight of the total composition, i.e, in amounts that are sufficient to provide the desired unit dosage. It may exist in different polymorphic forms, i.e. different crystalline forms.

For purposes of oral administration, tablets containing various excipients such as sodium citrate, calcium carbonate and calcium phosphate may be employed along with various disintegrants such as starch, preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred fillers would also include lactose or milk sugar as well as high molecular weight polyethylene glycols. When aqueous suspensions and/or elixirs are desired for oral administration, the sertraline, or pharmaceutically acceptable salt thereof, may be combined with various sweetening or flavoring agents, coloring matter or dyes and, if so desired, emulsifying and/or suspending agents, together with diluents such as water, ethanol, propylene glycol, glycerin and various like combinations thereof.

For purposes of parenteral administration, solutions of sertraline, or a pharmaceutically acceptable salt thereof, in sesame or peanut oil or in aqueous propylene glycol or N,N-dimethylformamide may be employed, as well as sterile aqueous solutions of the water-soluble, non-toxic mineral and organic acid addition salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

A typical dry solid pharmaceutical composition is prepared by blending the following materials together in the proportions by weight specified below:

| | |
|---|---|
| 1-(S)-cis-N-methyl-4-(3,4-dichlorophenyl)-1, 2,3,4-tetrahydro-1-naphthalenamine hydrochloride: | 50 |
| Sodium citrate: | 25 |
| Alginic acid: | 10 |
| Polyvinylpyrrolidone: | 10 |
| Magnesium stearate: | 5 |

After the dried composition is thoroughly blended, tablets are punched from the resulting mixture, each tablet being of such size that it contains 100mg of sertraline hydro-chloride. Other tablets are also prepared in a similar fashion containing 5, 10, 25, 50, 150 and 200mg of sertraline hydrochloride, respectively, by using the appropriate amount of the naphthalenamine salt in each case.

Another typical dry solid pharmaceutical composition is prepared by combining the following materials together in the proportions by weight indicated below:

| | |
|---|---|
| 1-(S)-cis-N-methyl-4-(3,4-dichlorophenyl)-1, 2,3,4-tetrahydro-1-naphthalenamine hydrochloride: | 55.950 |
| Calcium Hydrogen Phosphate, Ph. Eur. | 24.000 |
| Microcrystalline Cellulose, Ph. Eur. | 44.925 |
| Hydroxypropyl Cellulose, NF | 4.500 |
| Sodium Starch Glycollate, BP | 18.750 |
| Magnesium Stearate, Ph. Eur. | 1.875 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 50mg of the active ingredient.

The following examples illustrate, but do not limit the scope of the present invention.

EXAMPLE 1

Sertraline Hydrochloride—Form I

To a 12 liter, 3 neck round-bottom flask equipped with a mechanical stirrer, a thermometer and a nitrogen atmosphere, 443ml of isopropanol and 1477 grams of sertraline hydrochloride were combined. The resulting white slurry was stirred for 112 hours at 25° C. The slurry was filtered and washed with 2×250ml of isopropanol and dried at 45° to 50° C. under vacuum to yield desired polymorph (Form I).

EXAMPLE 2

Sertraline Hydrochloride—Form I

To a 12 liter, 3 neck round-bottom flask equipped with mechanical stirrer, 4287ml of methylene chloride, 2553ml water and 638.3gms sertraline mandelate were combined. A 10% sodium hydroxide solution, 383ml, was then added and the resulting two clear layers were separated. The aqueous layer was further extracted with 2×586ml of methylene chloride. The combined methylene chloride layers were washed with 2×1110ml water and separated. The methylene chloride solution was atmospherically distilled and displaced with isopropanol to a final volume of 4440ml. 53.7ml water were added to the resulting isopropanol solution. The solution was cooled to 50° C. and seeded with sertraline hydrochloride - Form I. Hydrogen chloride, 208.1ml of 6.37 molar, in aqueous isopropanol was added to the clear solution to give a thick white slurry. Additional isopropanol 1500ml was added and the material stirred for three hours at 50° C., then cooled to room temperature overnight. The solution was distilled at atmospheric pressure to remove 1,900ml. Isopropanol was then added (1000ml) to lower the water content. The mixture was then cooled and filtered to yield desired crystalline polymorph (Form I).

EXAMPLE 3

Sertraline Hydrochloride—Form I

To a 12 liter, 3 neck round-bottom flask equipped with mechanical stirrer, 2900ml of ethyl acetate, 2900ml water and 446.1gms of sertraline mandelate salt were combined. Sodium bicarbonate, 107 grams and 3560ml of saturated sodium bicarbonate solution were then added and the resulting two essentially clear layers were separated. The aqueous layer was further extracted with 4×740ml of ethyl acetate. The combined ethyl acetate layers were washed with 3×750ml water, 900ml of brine and separated. The ethyl acetate solution was atmospherically distilled and displaced with hexanes to a final volume of 2700ml. The solution was cooled to 50° C. and seeded with sertraline hydrochloride. Concentrated hydrochloric acid, 89.2ml, was added to the clear solution to give a thick white slurry. The mixture was then cooled, stirred overnight and filtered to yield desired crystalline polymorph (Form I).

EXAMPLE 4

Sertraline Hydrochloride—Form I

To a 12 liter, 3 neck round-bottom flask equipped with mechanical stirrer, 2900ml of ethyl acetate, 2900ml water and 446.1gms of sertraline mandelate were combined. Solid sodium bicarbonate, 127gms, and 3560ml of saturated sodium bicarbonate solution were then added and the resulting two essentially clear layers were separated. The aqueous layer was further extracted with 4×750ml of ethyl acetate. The combined ethyl acetate layers were washed with 5×1000ml water, 1000ml of brine and separated. The ethyl acetate solution was concentrated by distillation at atmospheric pressure to a final volume of 3560ml. The solution was cooled to 58° C. and seeded with sertraline hydrochloride. Concentrated hydrochloric acid, 81.1ml, was added to the clear solution to give a thick white slurry. The mixture was then cooled, stirred overnight and filtered to yield desired crystalline polymorph (Form I).

We claim:

1. A crystalline polymorph of the hydrochloride salt of (1S-cis)-4-(3,4-dichlorophenyl)-1,2,3,4-tetrahydro-N-methyl-1-naphthalenamine that exhibits an X-ray powder diffraction pattern having characteristic peaks expressed in degrees 2 $\theta$ at approximately 7.1, 12.7, 14.1, 15.3, 15.7, 21.2 23.4 and 26.3.

2. A crystalline polymorph of the hydrochloride salt of (1S-cis)-4-(3,4-dichlorophenyl)-1,2,3,4-tetrahydro-N-methyl-1-naphthalenamine that exhibits an infrared absorption spectrum in potassium bromide having characteristic absorption bands expressed in reciprocal centimeters at approximately:

3100–3000 (W)*; 3000–2800(m)*, 2710–2500(m); 2500–2450(m); 1585(m); 1560(m); 1470–1450 (s)*; 1400(s), 1430(m); 1375(m); 1340(m) 1215(m); 1135(s); 1060(m); 1030(m); 1015(m); 955(m); 930(m); 920(m); 825(s); 800(s); 790(s); 760(s); 710(m); 700(s); 670(s); $\neq$*(w) = weak intensity; (m) = medium intensity; (s) = strong intensity.

3. A crystalline polymorph of the hydrochloride salt of (1S-cis)-4-(3,4-dichlorophenyl)-1,2,3,4-tetrahydro-N-methyl-1-naphthalenamine according to claim 1 that exhibits an infrared absorption spectrum in potassium bromide having characteristic absorption bands expressed in reciprocal centimeters at approximately:

3100–3000(w)*; 3000–2800(m)*, 2710–2500(m); 2500–2450(m); 1585(m); 1560(m); 1470–1450(s)*; 1400(s), 1430(m); 1375(m); 1340(m) 1215(m); 1135(s); 1060(m); 1030(m); 1015(m); 955(m); 930(m); 920(m); 825(s); 800(s); 790(s); 760(s); 710(m); 700(s); 670(s); $\neq$*(w) = weak intensity; (m) = medium intensity; (s) = strong intensity.

Figure 3:
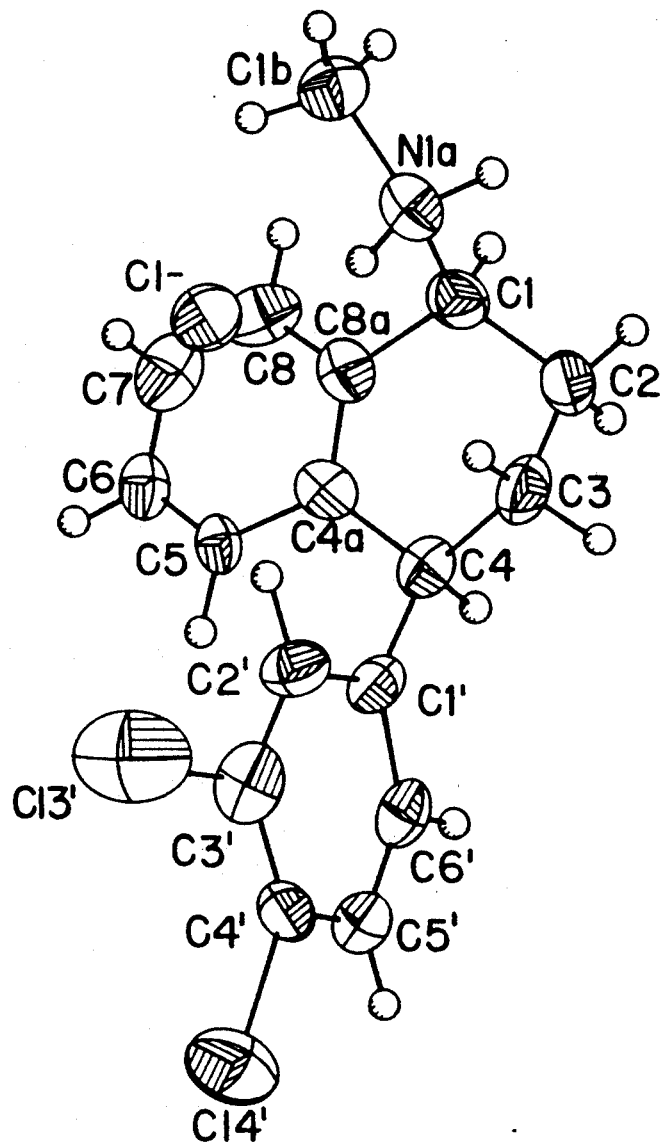
FIG. 3 depicts the absolute configuration of Form I as derived from single crystal X-ray. (Atomic coordinates based on Tables 3-7).

4. A crystalline polymorph of the hydrochloride salt of (1S-cis)-4-(3,4-dichlorophenyl)-1,2,3,4-tetrahydro-N-methyl-1-naphthalenamine that exhibits a single crystal X-ray crystallographic analysis with (a) crystal parameters that are approximately equal to the following:

| | |
|---|---|
| crystal size (mm) | 0.11 × 0.11 × 0.12 |
| cell dimensions | a = 8.004(5)Å |
| ( = Angstrom | b = 8.372(5)Å |
| ° = degree) | c = 25.21(2)Å |
| | α = 90.00° |
| | β = 90.00° |
| | γ = 90.00° |
| | V = 1689.3(6)A$^3$ |
| Space group | P2$_1$2$_1$2$_1$ |
| | Orthorombic |
| Molecules/unit cell | 4 |
| density (g/cm$^3$) | 1.354. | wherein a, b and c and α, β and γ are as previously defined; and (b) atomic positions of all atoms relative to the origin of the unit cell as recited in Tables 3 and 7, and as represented in FIG. 3.

5. A crystalline polymorph of the hydrochloride salt of (1S-cis)-4-(3,4-dichlorophenyl)-1,2,3,4-tetrahydro-N-methyl -1-naphthalenamine according to claim 1 that exhibits a single crystal X-ray crystallographic analysis with (a) crystal parameters that are approximately equal to the following:

| | |
|---|---|
| crystal size (mm) | 0.11 × 0.11 × 0.12 |
| cell dimensions | a = 8.004(5)Å |
| (Å = Angstrom | b = 8.372(5)Å |
| ° = degree) | c = 25.21(2)Å |
| | α = 90.00° |
| | β = 90.00° |
| | γ = 90.00° |
| | V = 1689.3(6)A$^3$ |
| Space group | P2$_1$2$_1$2$_1$ |
| | Orthorombic |
| Molecules/unit cell | 4 |
| density (g/cm$^3$) | 1.354. | wherein a, b and c and α, β and γ are as previously defined; and (b) atomic positions of all atoms relative to the origin of the unit cell as recited in Tables 3 and 7, and as represented in FIG. 3.

6. A crystalline polymorph of the hydrochloride salt of (1S-cis)-4-(3,4-dichlorophenyl)-1,2,3,4-tetrahydro-N-methyl-1-naphthalenamine according to claim 2 that exhibits a single crystal X-ray crystallographic analysis with (a) crystal parameters that are approximately equal to the following:

|  |  |
|---|---|
| crystal size (mm) | 0.11 × 0.11 × 0.12 |
| cell dimensions | a = 8.004(5)Å |
| (Å = Angstrom | b = 8.372(5)Å |
| ° = degree) | c = 25.21(2)Å |
|  | α = 90.00° |
|  | β = 90.00° |
|  | γ = 90.00° |
|  | V = 1689.3(6)Å$^3$ |
| Space group | P2$_1$2$_1$2$_1$ |
|  | Orthorombic |
| Molecules/unit cell | 4 |
| density (g/cm$^3$) | 1.354, | wherein a, b and c and α, β and γ are as previously defined; and (b) atomic positions of all atoms relative to the origin of the unit cell as recited in Tables 3 and 7, and as represented in FIG. 3.

7. A crystalline polymorph of the hydrochloride salt of (1S-cis)-4-(3,4-dichlorophenyl)-1,2,3,4-tetrahydro-N-methyl-1-naphthalenamine according to claim 3 that exhibits a single crystal X-ray crystallographic analysis with (a) crystal parameters that are approximately equal to the following:

|  |  |
|---|---|
| crystal size (mm) | 0.11 × 0.11 × 0.12 |
| cell dimensions | a = 8.004(5)Å |
| (Å = Angstrom | b = 8.372(5)Å |
| ° = degree) | c = 25.21(2)Å |
|  | α = 90.00° |
|  | β = 90.00° |
|  | γ = 90.00° |
|  | V = 1689.3(6)Å$^3$ |
| Space group | P2$_1$2$_1$2$_1$ |
|  | Orthorombic |
| Molecules/unit cell | 4 |
| density (g/cm$^3$) | 1.354, | wherein a, b and c and α, β and γ are as previously defined; and (b) atomic positions of all atoms relative to the origin of the unit cell as recited in Tables 3 and 7, and as represented in FIG. 3.

8. A pharmaceutical composition comprising an amount of a polymorph according to claim 1 effective in treating depression, anxiety-related disorders, obesity, chemical dependencies or addictions orpremature ejaculation in a human, and a pharmaceutically acceptable carrier.

9. A pharmaceutical composition comprising an amount of a polymorph according to claim 2 effective in treating depression, anxiety-related disorders, obesity, chemical dependencies or addictions or premature ejaculation in a human, and a pharmaceutically acceptable carrier.

10. A pharmaceutical composition comprising an amount of a polymorph according to claim 4 effective in treating depression, anxiety-related disorders, obesity, chemical dependencies or addictions or premature ejaculation in a human, and a pharmaceutically acceptable carrier.

11. A pharmaceutical composition comprising an amount of a polymorph according to of claim 7 effective in treating depression, anxiety-related disorders, obesity, chemical dependencies or addictions or premature ejaculation in a human, and a pharmaceutically acceptable carrier.

12. A method of treating a condition selected from depression, anxiety-related disorders, obesity, chemical dependencies and addictions and premature ejaculation in a human, comprising administering to said human an amount of a polymorph according to claim 1 effective in treating such condition.

13. A method of treating a condition selected from depression, anxiety-related disorders, obesity, chemical dependencies and addictions and premature ejaculation in a human, comprising administering to said human an amount of a polymorph according to claim 2 effective in treating such condition.

14. A method of treating a condition selected from depression, anxiety-related disorders, obesity, chemical dependencies and addictions and premature ejaculation in a human, comprising administering to said human an amount of a polymorph according to claim 4 effective in treating such condition.

15. A method of treating a condition selected from depression, anxiety-related disorders, obesity, chemical dependencies and addictions and premature ejaculation in a human, comprising administering to said human an amount of a polymorph according to claim 7 effective in treating such condition.

* * * * *